(12) United States Patent
Saberi et al.

(10) Patent No.: US 12,156,763 B2
(45) Date of Patent: Dec. 3, 2024

(54) WEARABLE ULTRASOUND SYSTEM AND METHOD

(71) Applicant: iSono Health, Inc., San Francisco, CA (US)

(72) Inventors: Shadi Saberi, San Francisco, CA (US); Maryam Ziaei, San Francisco, CA (US); Chris Tacklind, San Francisco, CA (US); Jeff Schlosser, San Francisco, CA (US)

(73) Assignee: iSono Health, Inc., South San Francisco, CA (US)

( * ) Notice: Subject to any disclaimer, the term of this patent is extended or adjusted under 35 U.S.C. 154(b) by 0 days.

(21) Appl. No.: 18/168,160

(22) Filed: Feb. 13, 2023

(65) Prior Publication Data

US 2023/0190232 A1 Jun. 22, 2023

Related U.S. Application Data

(63) Continuation of application No. 15/465,251, filed on Mar. 21, 2017, now Pat. No. 11,576,650.
(Continued)

(51) Int. Cl.
*A61B 8/00* (2006.01)
*A61B 8/08* (2006.01)
(Continued)

(52) U.S. Cl.
CPC .......... *A61B 8/4209* (2013.01); *A61B 8/0825* (2013.01); *A61B 8/145* (2013.01);
(Continued)

(58) Field of Classification Search
CPC ..... A61B 8/4209; A61B 8/0825; A61B 8/145; A61B 8/4254; A61B 8/4263;
(Continued)

(56) References Cited

U.S. PATENT DOCUMENTS

| | | | |
|---|---|---|---|
| 4,186,747 A | * | 2/1980 | Iinuma ................. A61B 8/0825 128/915 |
| 4,206,763 A | | 6/1980 | Pedersen |

(Continued)

FOREIGN PATENT DOCUMENTS

| | | |
|---|---|---|
| CN | 102316791 A | 1/2012 |
| CN | 103415258 A | 11/2013 |

(Continued)

OTHER PUBLICATIONS

Extended European Search Report for Application No. 17770996.1, dated Dec. 9, 2019.
(Continued)

*Primary Examiner* — Bo Joseph Peng
(74) *Attorney, Agent, or Firm* — WILSON SONSINI GOODRICH & ROSATI

(57) ABSTRACT

An ultrasound system including: a scanner module including a housing including a first fastener element, an ultrasound transducer, a rotational actuator, and an electronics module; and a positioner module including a second fastener element; operable between a first mode, wherein the first and second fastener elements cooperatively couple the scanner module to the positioner module, and a second mode, wherein the scanner module and positioner modules are separate. An ultrasound system including: a housing including a handle region and a membrane; an ultrasound transducer; a reservoir; a rotational actuator; and an electronics module.

14 Claims, 16 Drawing Sheets

Related U.S. Application Data

(60) Provisional application No. 62/311,110, filed on Mar. 21, 2016.

(51) Int. Cl.
*A61B 8/14* (2006.01)
*G01N 29/265* (2006.01)
*G01S 7/52* (2006.01)
*G01S 15/89* (2006.01)

(52) U.S. Cl.
CPC .......... *A61B 8/4254* (2013.01); *A61B 8/4263* (2013.01); *A61B 8/4281* (2013.01); *A61B 8/4411* (2013.01); *A61B 8/4427* (2013.01); *A61B 8/4455* (2013.01); *A61B 8/4461* (2013.01); *A61B 8/4488* (2013.01); *A61B 8/4494* (2013.01); *G01N 29/265* (2013.01); *G01S 7/52079* (2013.01); *G01S 15/8915* (2013.01); *G01S 15/8922* (2013.01); *G01S 15/8936* (2013.01); *G01S 15/894* (2013.01); *G01S 15/8993* (2013.01); *G01S 7/52084* (2013.01); *G01S 15/899* (2013.01)

(58) Field of Classification Search
CPC ... A61B 8/4281; A61B 8/4411; A61B 8/4427; A61B 8/4455; A61B 8/4461; A61B 8/4488; A61B 8/4494; G01N 29/265; G01S 7/52079; G01S 15/8915; G01S 15/8922; G01S 15/8936; G01S 15/894; G01S 15/8993; G01S 7/52084; G01S 15/899
See application file for complete search history.

(56) References Cited

U.S. PATENT DOCUMENTS

| | | | |
|---|---|---|---|
| 6,117,080 | A | 9/2000 | Schwartz |
| 6,478,739 | B1 | 11/2002 | Hong |
| 6,482,158 | B2 | 11/2002 | Mault |
| 6,524,250 | B1 | 2/2003 | Weber et al. |
| 7,556,602 | B2 | 7/2009 | Wang et al. |
| 7,771,360 | B2 | 8/2010 | Johnson et al. |
| 8,206,307 | B2 | 6/2012 | Barnard et al. |
| 8,298,146 | B2 | 10/2012 | Amara et al. |
| 8,323,201 | B2 | 12/2012 | Towfiq et al. |
| 2002/0042574 | A1* | 4/2002 | Manor ................ A61B 8/4461 600/454 |
| 2004/0153008 | A1* | 8/2004 | Sharf ................... A61B 8/4472 600/588 |
| 2006/0094988 | A1* | 5/2006 | Tosaya ................... A61N 7/00 601/2 |
| 2006/0191344 | A1 | 8/2006 | Hashimoto |
| 2007/0032726 | A1 | 2/2007 | Osaka et al. |
| 2008/0269613 | A1 | 10/2008 | Summers et al. |
| 2008/0281237 | A1 | 11/2008 | Slayton et al. |
| 2009/0177083 | A1 | 7/2009 | Matsumura |
| 2009/0259128 | A1 | 10/2009 | Stribling |
| 2010/0036243 | A1* | 2/2010 | Matsumura .......... A61B 8/4281 600/443 |
| 2010/0156404 | A1* | 6/2010 | Han ..................... A61B 8/4461 324/251 |
| 2010/0168577 | A1* | 7/2010 | Vezina .................... A61B 8/00 600/443 |
| 2011/0040187 | A1* | 2/2011 | Matsumura .......... A61B 5/6843 600/443 |
| 2011/0218423 | A1 | 9/2011 | Hsieh et al. |
| 2013/0267850 | A1 | 10/2013 | Berman |
| 2013/0289381 | A1 | 10/2013 | Oraevsky et al. |
| 2015/0209016 | A1 | 7/2015 | Lefebvre et al. |
| 2016/0354058 | A1 | 12/2016 | Schlosser et al. |

FOREIGN PATENT DOCUMENTS

| | | |
|---|---|---|
| DE | 3224290 A1 | 12/1983 |
| JP | 2015116215 A | 6/2015 |
| WO | WO-2014016663 A1 | 1/2014 |
| WO | 2015073523 A1 | 5/2015 |
| WO | WO-2015085257 A1 | 6/2015 |

OTHER PUBLICATIONS

Chinese Patent Application No. 201780030865.4 Office Action dated Dec. 3, 2021.
Chinese Patent Application No. 201780030865.4 Office Action dated Feb. 22, 2021.
Chinese Patent Application No. 201780030865.4 Office Action dated May 23, 2022.
PCT/US2017/023427 International Preliminary Report on Patentability dated Oct. 4, 2018.
PCT/US2017/023427 International Search Report and Written Opinion dated May 25, 2017.
U.S. Appl. No. 15/465,251 Notice of Allowance dated Sep. 23, 2022.
U.S. Appl. No. 15/465,251 Office Action dated Feb. 14, 2020.
U.S. Appl. No. 15/465,251 Office Action dated Feb. 23, 2022.
U.S. Appl. No. 15/465,251 Office Action dated Jul. 12, 2021.
U.S. Appl. No. 15/465,251 Office Action dated Nov. 30, 2020.

* cited by examiner

WEARABLE ULTRASOUND SYSTEM AND METHOD

CROSS-REFERENCE TO RELATED APPLICATIONS

This application is a continuation of U.S. application Ser. No. 15/465,251, filed Mar. 21, 2017, which issued as U.S. Pat. No. 11,576,650 on Feb. 14, 2023, which in turn claims the benefit of U.S. Provisional Application Ser. No. 62/311,110, filed on Mar. 21, 2016, which is incorporated in its entirety by this reference.

TECHNICAL FIELD

This invention relates generally to the medical field, and more specifically to an improved wearable ultrasound system and method in the medical field.

BACKGROUND

Breast cancer is the most commonly diagnosed cancer in women and produces the second highest death rate, second only to lung cancer. Early detection of breast cancer and other types of cancer is typically an important factor to successfully treat cancer. However, there are several reasons that, for some cancer patients, the disease is not detected early. One reason contributing to later detection of breast cancer is limited participation in breast tissue screening. Lower participation rates in annual screenings are partly due to limited access to the screening tool, (e.g., mammograms require specialized medical centers and highly trained staff), fear of radiation, and discomfort. Another reason is limitations in the performance of screening. For example, mammography (the current standard tool for breast screening) has low sensitivity for detection of cancer in patients with dense breast tissue, which leads to high false negative rates. Although magnetic resonance imaging (MRI) improves on some of the limitations of mammography by providing relatively comfortable, radiation-free imaging capability, MRI is prohibitively expensive for routine use and also has limited accessibility. Improved detection of cancer would decrease the percentage of breast cancer incidence at later stages. Currently, there is no good option for a low-cost, compact, and wearable ultrasound systems that can provide automated scanning of breast tissue (or other tissue) of an individual, to enable regular monitoring for early detection of cancer.

Thus, there is a need in the medical field to create an improved wearable ultrasound system and method. This invention provides such an improved system and method.

DESCRIPTION OF THE PREFERRED EMBODIMENTS

Figure 1A:
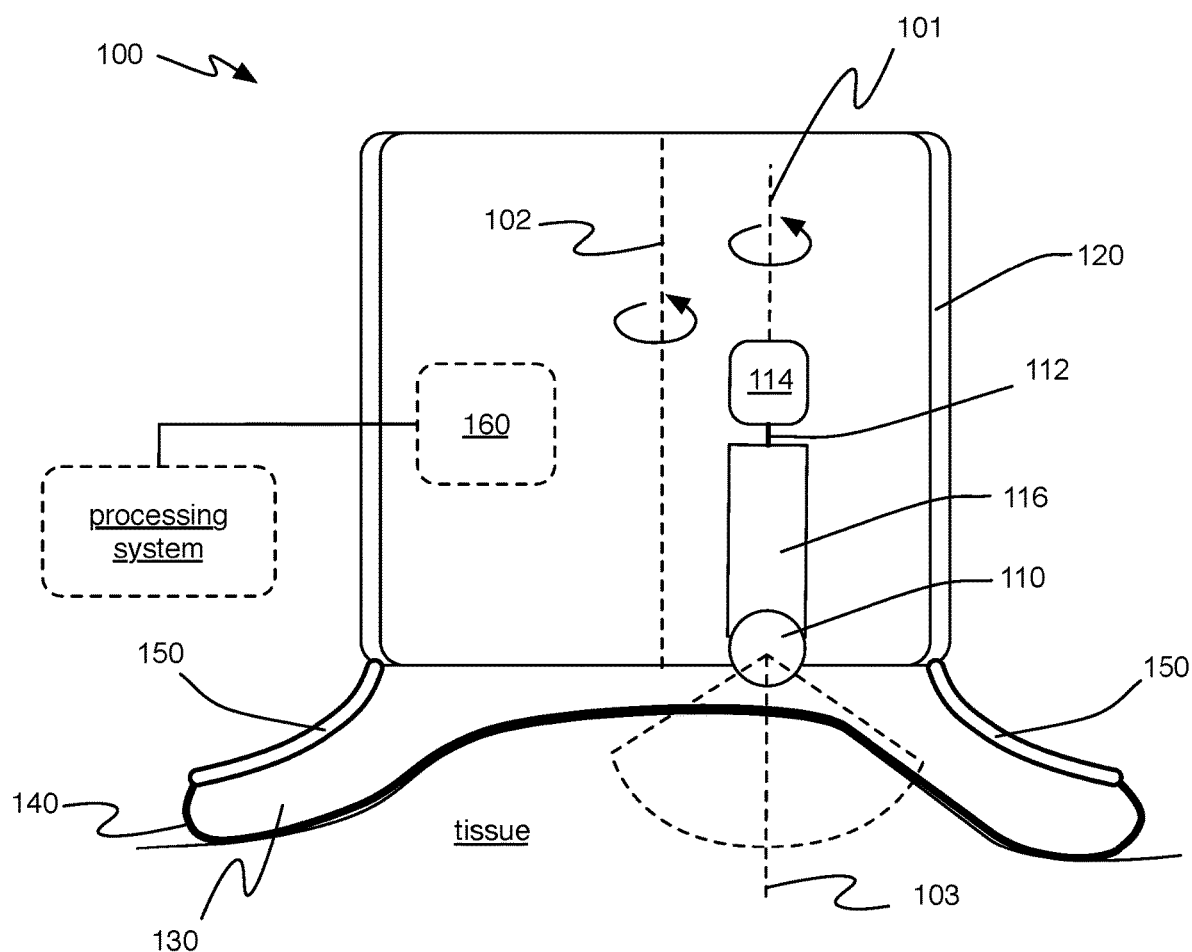
FIGS. 1A and 1B depict cross-sectional views of a first and second embodiment, respectively, of an ultrasound system.
Figure 1B:
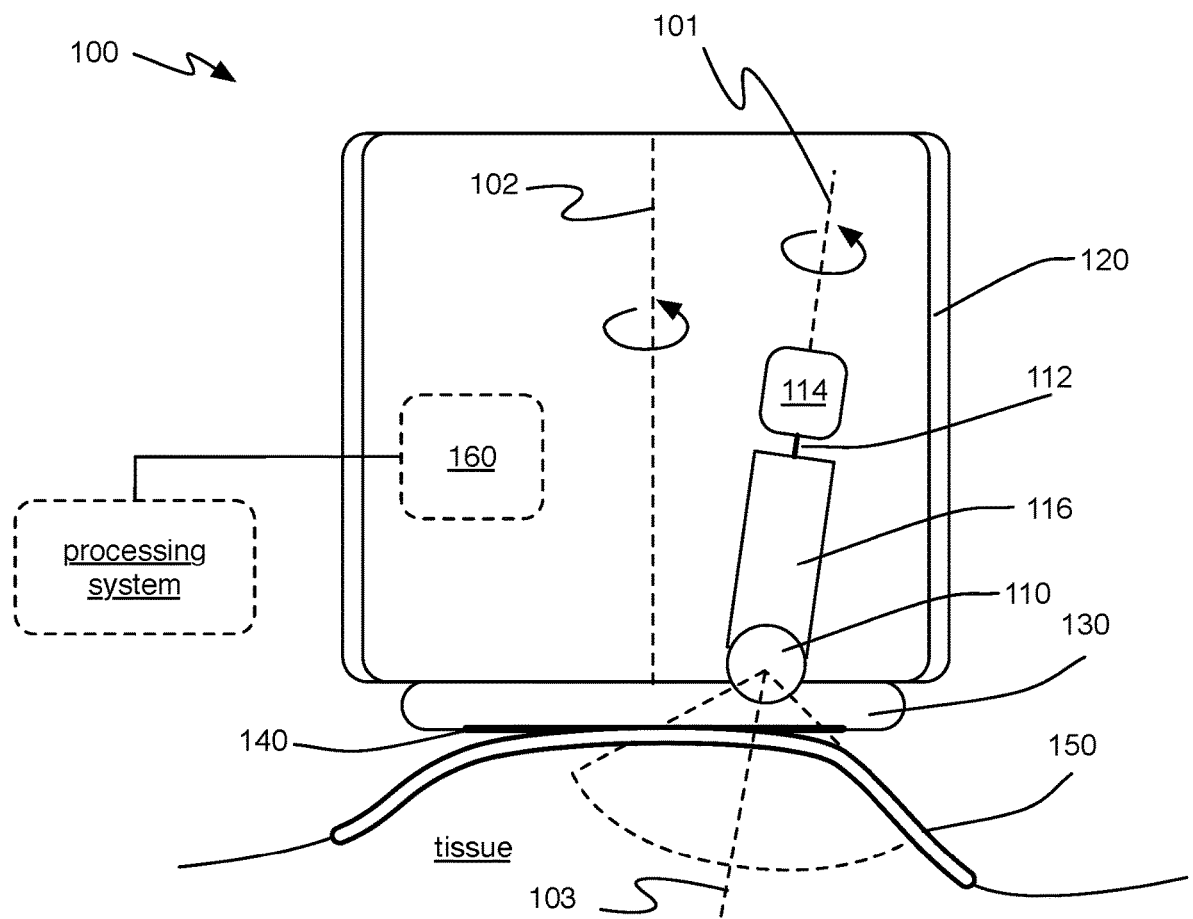

The following description of preferred embodiments of the invention is not intended to limit the invention to these preferred embodiments, but rather to enable any person skilled in the art to make and use this invention.

1. Wearable Ultrasound System

As shown in FIGS. 1A-1B and 2A-2B, an embodiment of an ultrasound system 100 can include: a scanner assembly including a transducer 110, preferably coupled to a shaft of an actuator by way of a transducer support, wherein the actuator provides rotation of the transducer support relative to a first axis 101 and/or translation of the transducer support; a housing 120 coupled to the transducer that preferably provides rotation of the transducer about a second axis 102 by way of a second actuator, wherein the first axis 101 is different from the second axis 102; a reservoir 130 of coupling medium surrounding a scanning portion of the transducer 110; a window 140, such as a membrane forming a boundary of the reservoir; a positioning portion 150, preferably configured to interface with the window for reliable and repeatable positioning of the scanner assembly relative to the body region of the user; and an electronics subsystem 160 configured to facilitate actuation of the transducer and acquisition of scanning data from the body region of the user.

The system 100 can function to provide a low-cost, compact, and/or wearable ultrasound system that can enable automated scanning of tissue of an individual, in order to promote regular monitoring for early detection of tissue anomalies. The system can include a compact mechanically driven transducer assembly integrated with ultrasound transmitter and receiver analog front-end (AFE) circuits, a field programmable gate array (FPGA) for digital signal processing, memory to store raw image data, and communication elements configured for communication and data transfer. However, the system 100 can additionally or alternatively include any other suitable components, as described in more detail below. The system 100 can be modular, thereby providing portions associated with enhanced comfort, washability, and/or wearability, and portions associated with data acquisition, data transmission, subsystem control, and/or data processing. As such, portions of the system 100 can be configured to be disposable, and other portions of the system can be configured to be substantially reusable, as described in more detail below.

In a specific application, the system 100 can at least partially comprise a wearable form factor adapted to scanning breast tissue of a patient, in order to promote regular monitoring for early detection of breast cancer. In more detail, the system 100 can be configured for scanning breast tissue of a user while the user is laying on his/her back, laying in a prone position, upright, and/or moving about in his/her daily life. The system 100 can additionally or alternatively be implemented in a clinical setting. The system 100 is preferably also a hands-free system, such that the system 100 can properly scan the tissue body of the user without the user or other operator holding onto the system. However, variations of the system 100 can be adapted to any other suitable tissue type, adapted for detection of any other suitable tissue anomaly, and/or adapted for any other suitable type of use. Furthermore, in a specific implementation, the system 100 can be configured to connect (e.g., using a wired connection, using a wireless connection) to a mobile computing device (e.g., smartphone, tablet, personal computer, wearable computing device, etc.) in a manner that allows a user to control or otherwise interact with the system 100, by way of an application executing at the mobile computing device. Thus, use of a mobile computing device and application can facilitate transfer of image data produced during scanning to a processing system (e.g., cloud computing system, remote server, etc.) for processing and reconstruction of 2D, 3D, and/or 4D (i.e., including time aspects) ultrasound images. Processing can additionally or alternatively include implementation of machine learning techniques to facilitate analysis and/or computer-aided detection of tumors and other tissue abnormalities over time. The system 100 and/or method 200 can also allow for sharing of image data (raw and/or processed) from users (e.g., with satisfaction of sensitive patient data handling and security requirements), for observation by one or more teleradiologists.

The system 100 is preferably configured to facilitate implementation of at least a portion of the method 200 described in Section 2 below; however, the system 100 can additionally or alternatively be configured to facilitate implementation of any other suitable method. Furthermore, while the system 100 and method 200 are primarily described in the context of ultrasound scanning, portions of the system 100 can additionally or alternatively be adapted with detection and/or emission elements associated with any other suitable scanning modality.

1.1 System—Transducer

The scanner assembly includes a transducer 110 coupled to a shaft of an actuator by way of a transducer support, wherein the actuator provides rotation of the transducer support relative to a first axis 101, wherein the transducer 110 functions to emit acoustic waves toward a tissue region of a user, and/or detect signals from the tissue region of the user resulting from interactions between the acoustic waves and the tissue region. The transducer 110 can include a single transducing element, or can alternatively include multiple transducing elements (e.g., arranged as an array). In variations wherein the transducer includes an array of elements, the elements can be arranged in a one-dimensional array (e.g., in a linear array), in a two-dimensional array (e.g., in a planar polygonal array, in a planar ellipsoidal array, in a planar circular array, in a planar-non-polygonal array), or in a three-dimensional array (e.g., in an array on a surface of a three-dimensional object). The transducing element(s) of the transducer 110 are preferably arranged at a distal region of the transducer 110 (e.g., at a tip region); however, the transducing elements can additionally or alternatively be arranged at any other suitable portion of the transducer 110 and/or any other suitable portion of the system 100. Furthermore, variations of a transducer 110 with multiple transducing elements can provide different focal lengths at each scan line and/or can enable beamforming and/or beam steering (e.g., by statically and/or dynamically offsetting the ultrasound phase and/or amplitude emitted from each element). Additionally or alternatively, implementation of a wideband transducer with one or more transducing elements can provide pulse echo data at different frequencies along each scan line, in order to improve axial and/or lateral resolution signal-to-noise ratios (SNRs) at different depths of the tissue body.

The transducing element(s) of the transducer 110 can include one or more piezoelectric transducing (PZT) elements (e.g., crystalline PZT elements, composite PZT elements, etc.), such that the transducer 110 is a PZT transducer. Additionally or alternatively, the transducing element(s) of the transducer 110 can include one or more piezoelectric micromachined ultrasonic transducing (PMUT) elements, such that the transducer 110 is a PMUT transducer (e.g., array of transducer elements). Additionally or alternatively, the transducing element(s) of the transducer 110 can include one or more capacitive micromachined ultrasonic transducing (CMUT) elements, such that the transducer 110 is a CMUT transducer. However, the transducer 110 can additionally or alternatively include any other suitable type of transducing element. Furthermore, the transducing elements of the transducer 110 can be configured to be selectively activated or activated for optimal imaging depending on the application, such as depending on the type or shape of object undergoing scanning.

The transducer 110 can provide amplitude (A-Mode) scanning data at each location along a scan path, in order to provide radiofrequency (RF) data and/or data indicative of quality-related metrics, from which features can be extracted to inform analyses of detected tissue abnormalities in the short and/or long term. Additionally or alternatively, the transducer can provide brightness-mode (B-mode) scanning data (e.g., upon conversion of raw ultrasound data) at each location along a scan path, wherein system elements associated with the scan path are described in more detail below. Such data can then be used by associated computing systems of the system 100 to generate processed image data, and/or to extract features associated with ultrasound reflection, ultrasound scattering, and/or ultrasound transmission (e.g., speed, attenuation, etc.). Additionally or alternatively, the ultrasound data can be processed by an external computing system (e.g., remote server). However, the transducer 110 can additionally or alternatively be configured to provide any other suitable type of scan, in order to generate 2D, 3D, and/or 4D ultrasound data.

Figure 3:
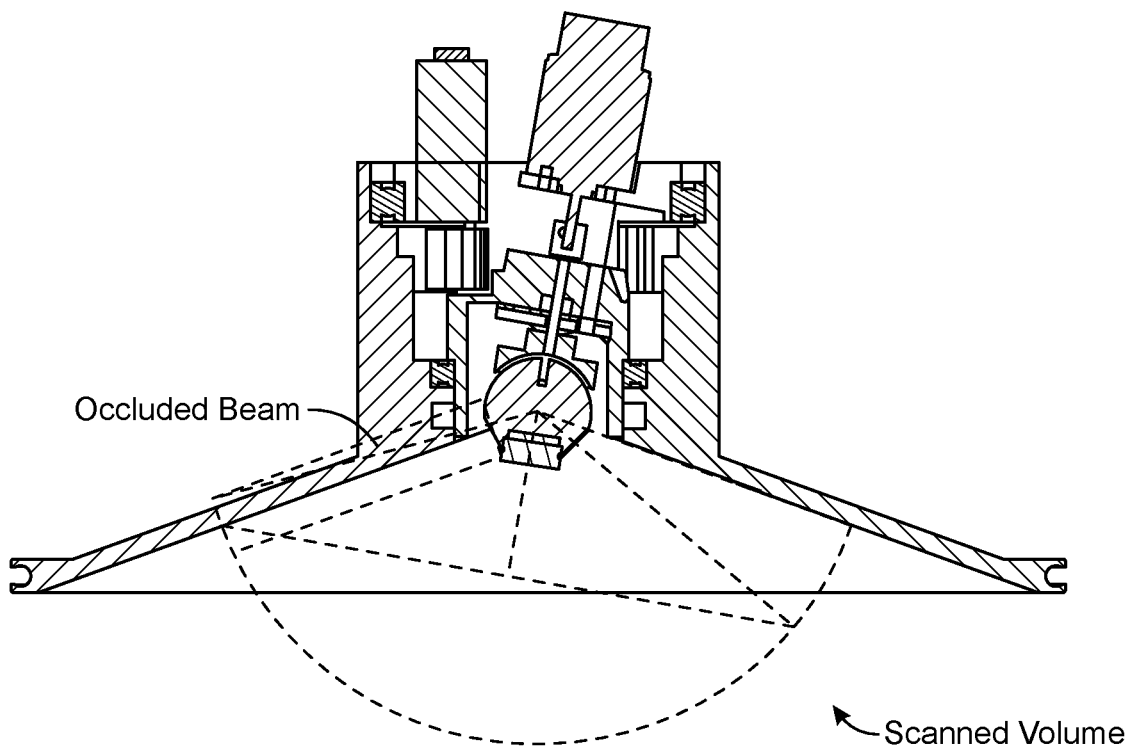
FIG. 3 depicts a cross-sectional view of a fourth specific example of portions of an ultrasound system and an example beam profile produced by the ultrasound system.

The ultrasound beam produced by one or more transducing elements of the transducer 110 can be defined by a width, a length of a Fresnel zone, and/or an angle of divergence, thereby producing an approximately fan-shaped profile, as shown in FIG. 1 and in the example of FIG. 3. Additionally or alternatively, the transducer 110 can have one or more of: focusing elements (e.g., an internal focusing element), acoustic lenses composed of materials that focus a beam by refraction, acoustic mirrors, electronic focusing elements, and/or any other suitable beam-shaping elements configured to adjust the beam profile emitted by the transducer 110. The ultrasound beam can additionally have any suitable frequency (fixed or adjustable), in order to adapt scanning to specific tissue types or scanning modes. Furthermore, the transducer 110 can alternatively be configured to provide any suitable number of ultrasound beams.

As shown in FIGS. 1A-1B and 2A-2D, the transducer 110 is preferably coupled to a shaft 112 or other coupler to an actuator 114, by way of a transducer support, wherein the actuator 114 provides rotation of the transducer support relative to a first axis 101. The shaft/coupler 112 preferably defines the first axis 101, and the transducer support 116 is coupled to the shaft/coupler 112 in order to provide a mechanism that produces motion of the transducer 110 in order to provide desired scanning behavior. In one variation, the transducer support includes a transmotion socket including a spherical portion interfacing with a concave plate, wherein the spherical portion includes a track (e.g., a circular track) and the concave plate includes a pin that engages the track during rotation of the shaft/coupler 112, in order to rotate the transducer 110 along an arc and/or translate the transducer. In a second variation, the actuator includes a linear actuator configured to translate the transducer (e.g., substantially tangent the user's tissue, substantially normal the central beam axis, substantially parallel the central beam axis, along an axis at an oblique angle to the central beam axis, etc.). For example, the linear actuator can produce radial transducer motion toward and away from one or more axes (e.g., second axis 102, such as described below). Alternative variations of the transducer support and/or actuator can however, produce any other suitable motion of the transducer 110 during scanning, based on one or more of: the morphology of the track, the morphology of the spherical portion (or alternatively, non spherical portion), the morphology of the plate, and the type of actuator (e.g., linear actuator).

Figure 2A:
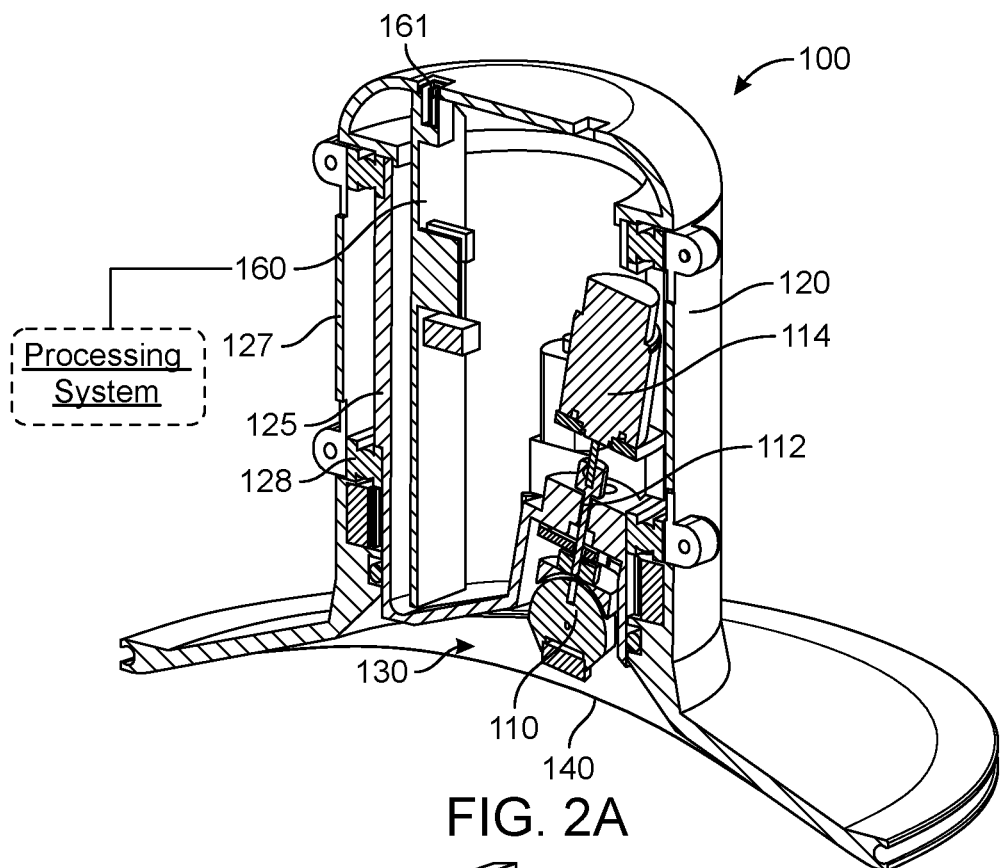
FIGS. 2A and 2B depict cross-sectional perspective views of a first specific example of an ultrasound system.
Figure 2B:
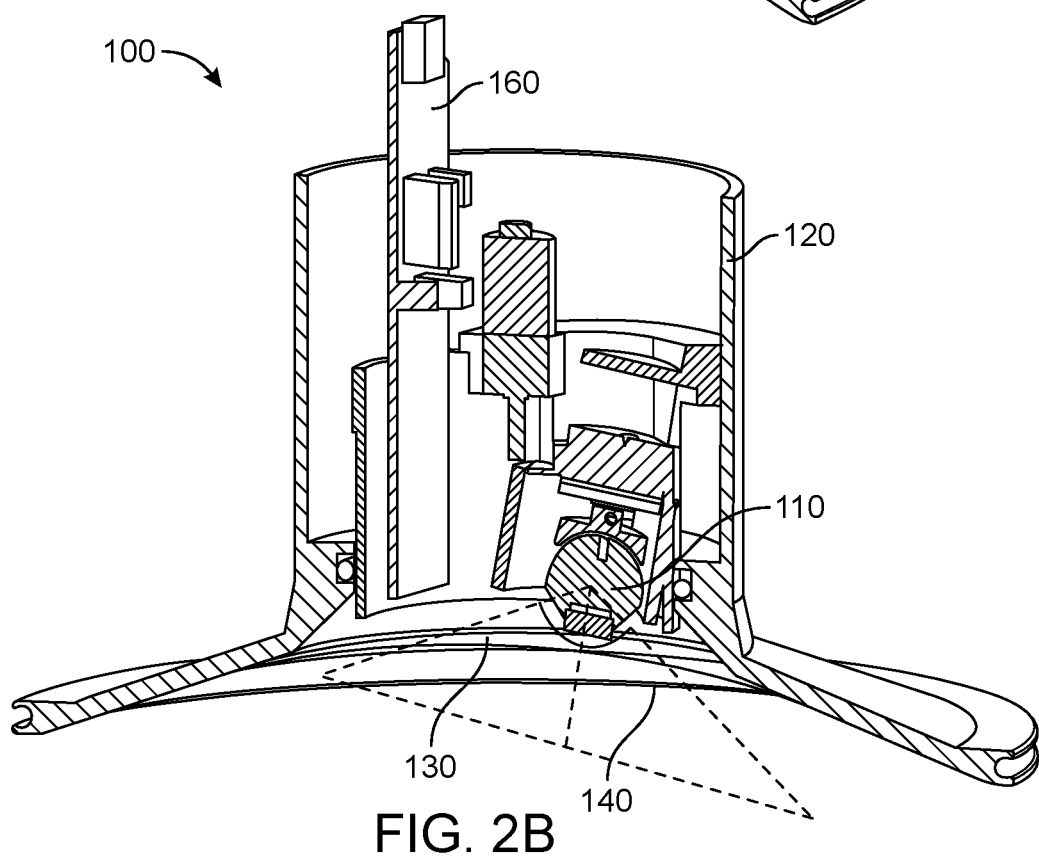
Figure 2C:
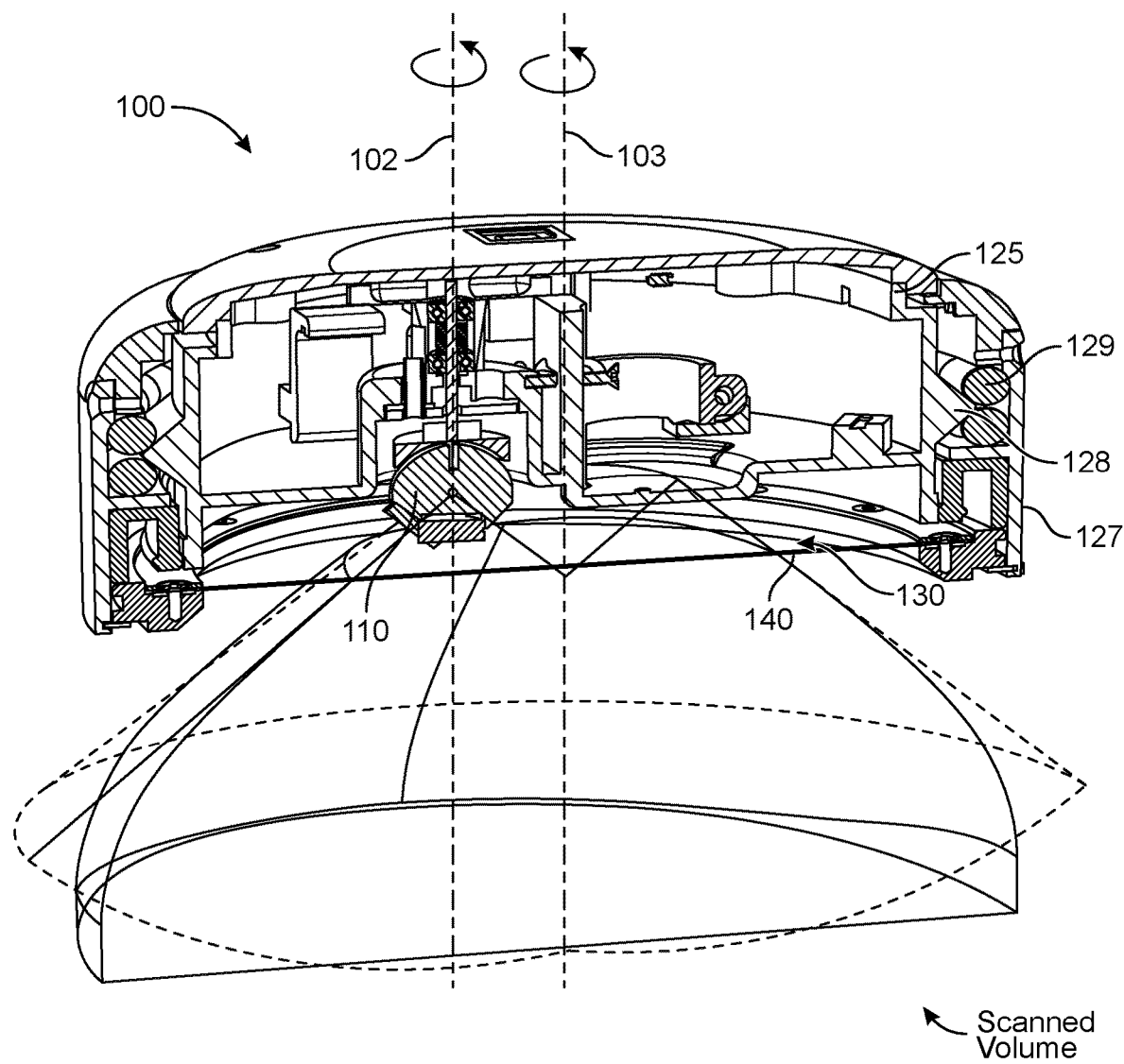
FIGS. 2C and 2D depict cross-sectional perspective views of a second and third specific example, respectively, of portions of an ultrasound system.
Figure 6:
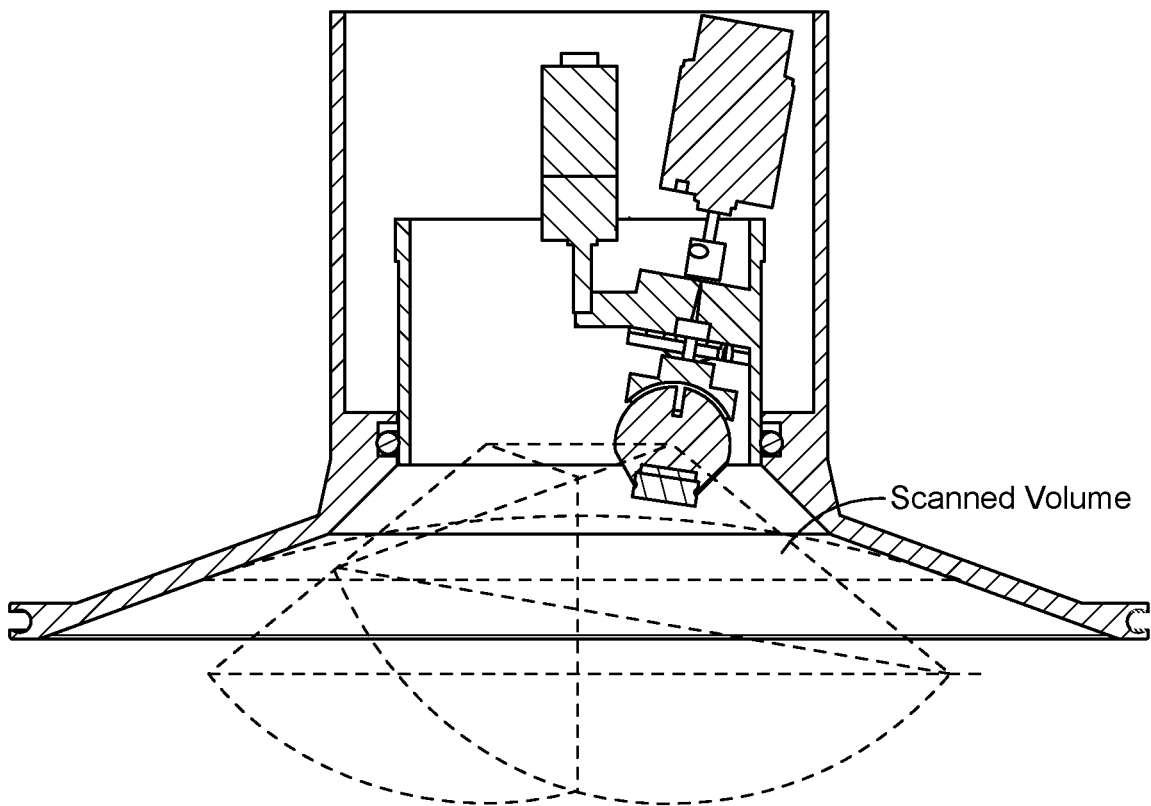
FIG. 6 depicts a cross-sectional view of a fifth specific example of portions of an ultrasound system and an example beam profile produced by the ultrasound system.

In relation to variations described above, rotation of the transducer support (e.g., and thereby of a fan-shaped beam profile of the transducer 110, such as shown in FIGS. 1A, 1B, 4A and 4B, and 7A) can be used to sweep a conical or frustoconical volume with the beam (e.g., as shown in FIGS. 2C, 3, and 6). Thus, the first axis 101 is preferably substantially aligned with the axis of symmetry of the fan-shaped beam, and/or can pass through the body of the transducer. However, the first axis 101 can alternatively be parallel to, but not aligned with an axis of symmetry of the beam produced by the transducer 110, can alternatively be perpendicular to an axis of symmetry of the beam produced by the transducer, or can alternatively intersect the axis of symmetry of the beam produced by the transducer 110 at any suitable point. Furthermore, the first axis 101 may not pass through the body of the transducer 110.

The actuator 114 is preferably a motor powered and/or controlled by elements of the electronics subsystem 160 described below, but can alternatively comprise any other suitable actuator that provides rotation of the transducer 110 about one or more axes and/or translation of the transducer 110 along one or more axes.

Additionally or alternatively, the transducer 110 can be coupled to an actuator (e.g., linear actuator) that can adjust the position of the transducer in one or more directions, to adjust a focal length or position of the transducer 110 in relation to a tissue body. The linear actuator can translationally couple the transducer 110 (e.g., to the housing), enabling control of the transducer position along a translation axis (e.g., first axis 101, second axis 102, central beam axis 103, longitudinal axis, etc.). For instance, the transducer can be transitioned, during operation, between one or more extended configurations and one or more retracted configurations, along the first axis of rotation 101 defined by the shaft 112, such that the focal distance(s) of the beam produced by the transducer 110 can be adjustable in a desired manner during a scanning operation.

Figure 4A:
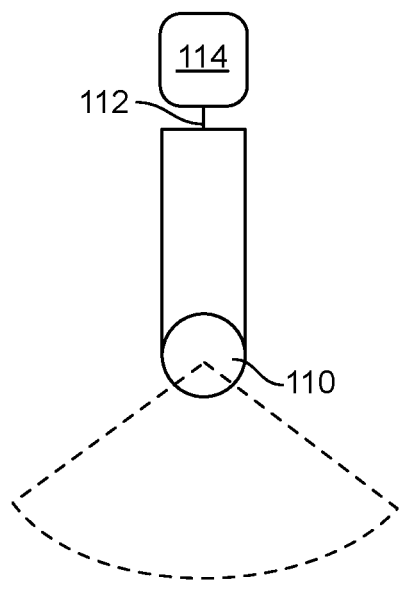
FIGS. 4A and 4B depict a variation a transducer in an ultrasound system, in a contracted and extended configuration, respectively.
Figure 4B:
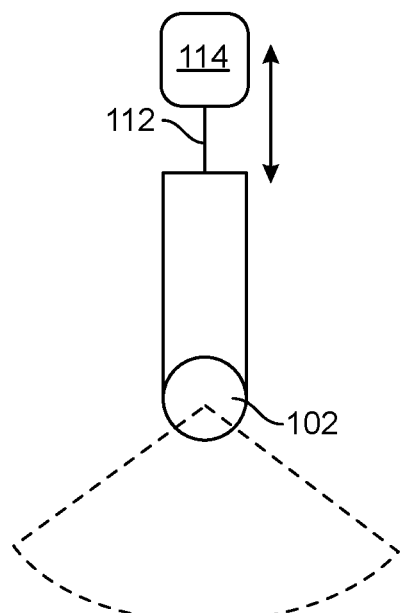

The linear actuator can control transducer 110 position relative to any other suitable elements of the system. In a first example, the linear actuator is arranged between the transducer 110 and the actuator 114 (e.g., translationally coupling the transducer 110 to the actuator 114), such as shown in FIGS. 4A and 4B. In a second example, the linear actuator is arranged between the actuator 114 and the first housing portion 125 (e.g., translationally coupling the transducer 110 and the actuator 114 to the first housing portion 125). In a third example, the linear actuator is arranged between the first 125 and second housing portions 127 (e.g., translationally coupling the transducer 110, actuator 114, and first housing portion 125 to the second housing portion 127). However, the linear actuator can have any other suitable arrangement.

The system 100 can additionally or alternatively include position sensors (e.g., mechanical stops, optical encoders, proximity sensors, etc.). The position sensors can enable (or assist) determination of transducer position, actuator position (e.g., rotational actuator, linear actuator, etc.), user tissue position (e.g., alignment relative to elements of the system such as the housing, transducer, etc.), and/or position of any other suitable elements of the system. In one example, each actuator of the system 100 can be associated with a corresponding encoder, enabling determination of the actuator positions (e.g., and thereby of the transducer position relative to the housing). In a second example, the system can include optical detectors configured to image and analyze the user's tissue (e.g., detecting nipple and/or areola alignment with respect to the system). However, the system can include any other suitable position sensors in any suitable arrangement.

The transducer 110 and/or any associated actuators can, however, be configured to modulate beam aspects in any other suitable manner.

1.2 System—Housing

The housing 120 is coupled to the transducer and functions to perform one or more of the following: provide rotation of the transducer about a second axis 102, wherein the first axis 101 is different from the second axis 102; protect and/or seal elements (e.g., electronic elements, as described in more detail below) of the system within a protective structure; enhance usability by a user in terms of form factor; and interface with other portions of the system 100 that are directly coupleable to the user (e.g., in modular formats of the system 100). The housing is preferably mostly substantially rigid in order to provide protection for internal components in a robust manner. However, one or more portions of the housing 120 can additionally or alternatively be flexible or compliant (e.g., in order to facilitate user handling and/or in order to provide user comfort). As described below, the housing 120 can include multiple portions, in order to facilitate performance of one or more functions noted above.

The housing 120 is preferably composed of a rigid material (e.g., a rigid plastic material, a metal, etc.), such that the housing 140 does not deform in response to normal forces, shear stresses, bending stresses, or torsional stresses induced during use of the system 100. Alternatively, as described briefly above, the housing 120 can be flexible to facilitate maintenance of compliance with a user as the user moves about (e.g., in variations wherein the system is used by the user while the user is in motion). In variations wherein the housing 120 is flexible, other elements of the system 100 can also be flexible (e.g., the electronics subsystem can comprise a flexible thin film battery, the electronics subsystem 160 can comprise flexible electronics, etc.) to facilitate compliance with the body of a user. In a specific example, the housing is composed of a plastic material (e.g., polycarbonate, acyrlonitrile butadiene styrene, polyethylene, etc.); however, variations of the specific example can alternatively be composed of any other suitable material.

Figure 5:
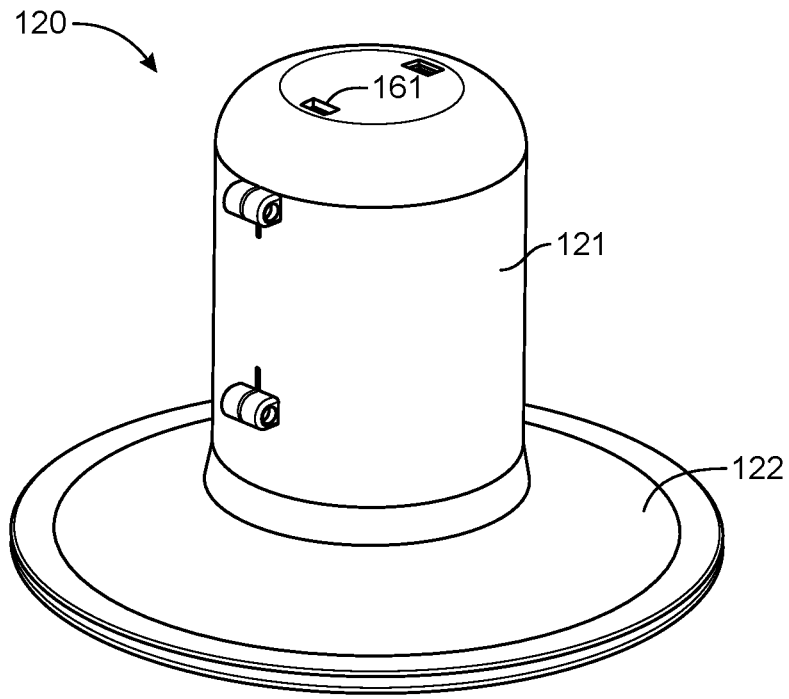
FIG. 5 depicts a perspective view of an example of a housing in a third embodiment of an ultrasound system.

As shown in FIGS. 2A, 2B, and 6, the housing 120 preferably has an external form factor that facilitates handling by the user and/or proper positioning of the system 100 relative to the user's body. As such, the housing 120 can have a handle region 121 configured to be grasped by a user or other operator, and a cupping region 122 configured to facilitate interfacing between the system 100 and the tissue region of the user. The handle region 121 can have features (e.g., grips, compliant regions, recessed regions, protrusions, etc.) that help the user or operator to grasp the housing. However, the handle region 121 can additionally or alternatively include any other suitable features. The cupping region 122 can have a morphology that accommodates the tissue of the user, wherein the morphology provides a concave portion to receive the tissue body; however, cupping region 122 can additionally or alternatively have any other suitable morphology. In a first variation, the housing is of unitary construction. In a second variation, the cupping region of the housing is separable from (e.g., repeatably connectable to and removable from) the handle region. However, the housing can have any other suitable configuration. In a specific example, as shown in FIG. 5, the handle region 121 is substantially cylindrical and is physically coextensive with the cupping region 122, which flares outward from the handle region 121 with a frustoconical surface. In the specific example, the cupping region 122 defines an internal concave surface configured to at least partially receive the tissue body (e.g., breast tissue) of the user for scanning by the transducer 110. Furthermore, the specific example and variations thereof can have dimensions that allow the housing to fit within a 15 cm×15 cm×25 cm volume (e.g., with a modular scanner diameter of 7 cm and a height of 10 cm). However, the housing 120 can additionally or alternatively have any other suitable external morphology (e.g., a morphology that omits a handle).

As noted above, the housing can have multiple portions, including a first housing portion 125 and a second housing portion 127 that interfaces with the first housing portion 125, such that the first housing portion 125 and the second housing portion 127 provide a mechanism that allows the transducer to rotate about a second axis 102, thereby allowing the transducer 110 to traverse a desired scanning path.

In more detail, the first housing portion 125 can be directly coupled to the transducer 110 at a region displaced from a longitudinal axis of the housing 110, such the transducer 110 is displaced from the longitudinal axis of the housing 120. In one variation, the transducer 110 can thus be coupled to the first housing portion 125 with a mount that positions the transducer 110 closer to an internal wall of the first housing portion 125 (i.e., a peripherally located transducer). In another variation, the transducer can be coupled to the first housing portion with a mount that positions the transducer 110 away from an internal wall of the first housing portion 125. In a specific example, as shown in FIGS. 2A and 2B, the first housing portion 125 includes an internal mount that is directly coupled to the actuator 114 (e.g., motor) coupled to the transducer 110 by way of a shaft 112, wherein the internal mount is located proximal an internal wall of the first housing portion 125; however, variations of the specific example can position the transducer 110 relative to any other suitable portion of the first housing portion 125.

In a specific example, in which the system additionally includes a linear actuator configured to provide radial motion with respect to the second axis, the combination of the linear actuator and the rotationally coupled housing portions can enable movement of the transducer to arbitrary positions within an area (e.g., a circle or annulus centered on and normal to the second axis).

While the variations and examples described above cover a configuration wherein the transducer 110 is housed within the first housing portion 125, alternative variations of the housing 120 can be configured such that the transducer 110 is at least partially situated outside the first housing portion 125.

The second housing portion 127 is configured to cooperate with the first housing portion 125 to provide a mechanism that allows the transducer to rotate about a second axis 102, thereby allowing the transducer 110 to traverse a desired scanning path. In one variation, the first housing portion 125 and the second housing portion 127 are concentrically aligned, and the second housing portion 127 provides a track along which a complementary portion of the first housing portion 125 can move during rotation of the first housing portion 125 relative to the second housing portion 127. In a first example, as shown in FIG. 2A the second housing portion 127 can include a track 128 that protrudes from an interior wall of the second housing portion 127, wherein the track 128 is complementary to a recessed portion of an exterior region of the first housing portion 125. In a variation of the first example, the second housing portion 127 can alternatively include a recessed track at an interior wall of the second housing portion 127, wherein the recessed track is complementary to a protruding portion of an exterior region of the first housing portion 125. However, still alternative versions of the above variations can be configured with any suitable number of tracks and/or tracks configured in any other suitable manner.

In the above described variations, the first housing portion 125 is preferably internal to the second housing portion 127, such that the first housing portion 125 rotates within the second housing portion. However, the first housing portion 125 can additionally or alternatively include portions that are exterior to the second housing portion 127, such that the first housing portion 125 rotates, at least in part, about the second housing portion 127. However, the first housing portion 125 and the second housing portion 127 can alternatively be oriented in any other suitable manner. For instance, the first housing portion 125 can interface with an inferior portion of the second housing portion 127 (e.g., in the orientation shown in FIGS. 2A and 2B), such that the track is a peripheral track between ends of the first housing portion 125 and the second housing portion 127. In relation to any tracks, the housing 120 can include any type of friction-reducer (e.g., ball bearings 129, lubricant, surface treatment, etc.) to provide smooth motion between the first housing portion 125 and the second housing portion 127. In specific examples, one of which is shown in FIG. 2C, the ball bearings used can have a large diameter (e.g., 0.25 cm to 1.5 cm in diameter) to prevent jamming or other undesired motion obstructions; however, the ball bearings used can have any other suitable morphology.

The system 100 can additionally include elements that provide automation of rotational motion and/or any other suitable type of motion between the first housing portion 125, the second housing portion 127, and/or the transducer 110. For instance, in some variations, the system 100 can include an actuator that drives rotational motion between the housing portions 125, 127. Similar to the actuator that rotates the transducer 110, the actuator that moves portions of the housing is preferably a motor powered and/or controlled by elements of the electronics subsystem 160 described below, but can alternatively comprise any other suitable actuator that provides rotation of the first housing portion 125 relative to the second housing portion 127 about one or more axes. In a specific example, the motor can drive a gear mechanism that transmits rotational motion from the motor to one or more gears that drive rotational motion between the housing portions; however, variations of the actuation system of the housing can alternatively transmit motion in any other suitable manner. The system can optionally include position sensors associated with the actuator (e.g., as discussed above regarding the transducer actuators).

Additionally or alternatively, the housing 120 can include an actuator that adjusts the position of the first housing portion 125 relative to the second housing portion 127 in one or more directions, in order to adjust a focal length or position of the transducer 110 in relation to a tissue body indirectly, by way of motion between portions of the housing 120. For instance, the first housing portion 125 and the second housing 127 interact with a screwing mechanism, such that rotation of the housing portions relative to each other produces translation of the first housing portion relative to the second housing portion. While actuated mechanisms are described above to provide automated motion between the first and the second housing portions 125, 127, generation of motion can alternatively be provided manually (e.g., by a user of the system, by an operator of the system). For instance, in one such variation, a user or operator can twist housing portions relative to each other, in order to provide motion. The system can optionally include position sensors associated with the actuator (e.g., as discussed above regarding the transducer actuators).

In relation to the axes of rotation of the transducer described above, the second axis of rotation 102 can be a longitudinal axis of the housing, as shown in FIG. 1. In relation to the first axis of rotation 101 of the transducer described above, the second axis of rotation 102 and the first axis of rotation 101 can have any suitable relationship that provides a desired scanning path and/or degree of spatial compounding with overlap in scanning regions as the transducer 110 traverses the scanning path, thereby reducing noise (e.g., speckle noise). For example, the second axis 102 can be arranged relative the transducer such that transducer rotation about the second axis causes it to sweep out a region such as an annular region (e.g., hollow cylinder, toroid, volume having an annular cross-section, etc.), disk-like or spheroidal region, and/or any other suitable region.

In a first variation, as shown in FIG. 3, the first axis of rotation 101 is tilted (e.g., at or less than an angle such as 5°, 10°, 20°, 30°, 45°, 60°, etc.) relative to the second axis of rotation 102, and orientated such that the transducer 110 is approximately perpendicular to the tissue being scanned at all times (e.g., to reduce glancing angle effects during scanning), wherein the scanning mechanism sweeps over a range (e.g., +/−60°) off axis in a plane. In this first variation, the tip of the transducer 110 (e.g., ball of the transducer) is approximately positioned at a central region of the scanning volume. In an example of this first variation, a 10° tilt between the first and the second axes produces a scan volume of 172.3 cm$^3$ and an overlapping scan volume of 93.5 cm$^3$ for spatial compounding.

To avoid occluded scanning beams at any phase of the scanning operation, an example of which is shown in FIG. 3, a second variation of the first variation can have a configuration where the tip of the transducer 110 (e.g., ball of the transducer) is displaced from a central region of the scanning volume. In a specific example, as shown in FIG. 6, the tip of the transducer 110 (e.g., ball of the transducer) is displaced from a central region of the scanning volume by 13 mm, which produces a 208.2 cm$^3$ scan volume, as shown in FIG. 6. However, to adjust the size and/or shape of the scan volume, one or more of the following system configurations can be implemented: the transducer beam can be configured to sweep over any other suitable range (e.g., +/−30° to)+/−90°; a tilt angle of the first axis of rotation 101 relative to the second axis 102 can be adjusted dynamically (e.g., using an actuator to adjust the tilt angle); a displacement position (e.g., position along a radial line) between the transducer and the second axis of rotation 102 can be dynamically adjusted; dimensions or morphology of the cupping region 122 of the housing 120 can be adjusted to avoid occlusion of the scan volume, a scanning depth parameter can be adjusted (e.g., extended), and coupling medium can be provided at desired locations (e.g., between portions of the housing and the window described below), such as shown in FIG. 1A.

Figure 2D:
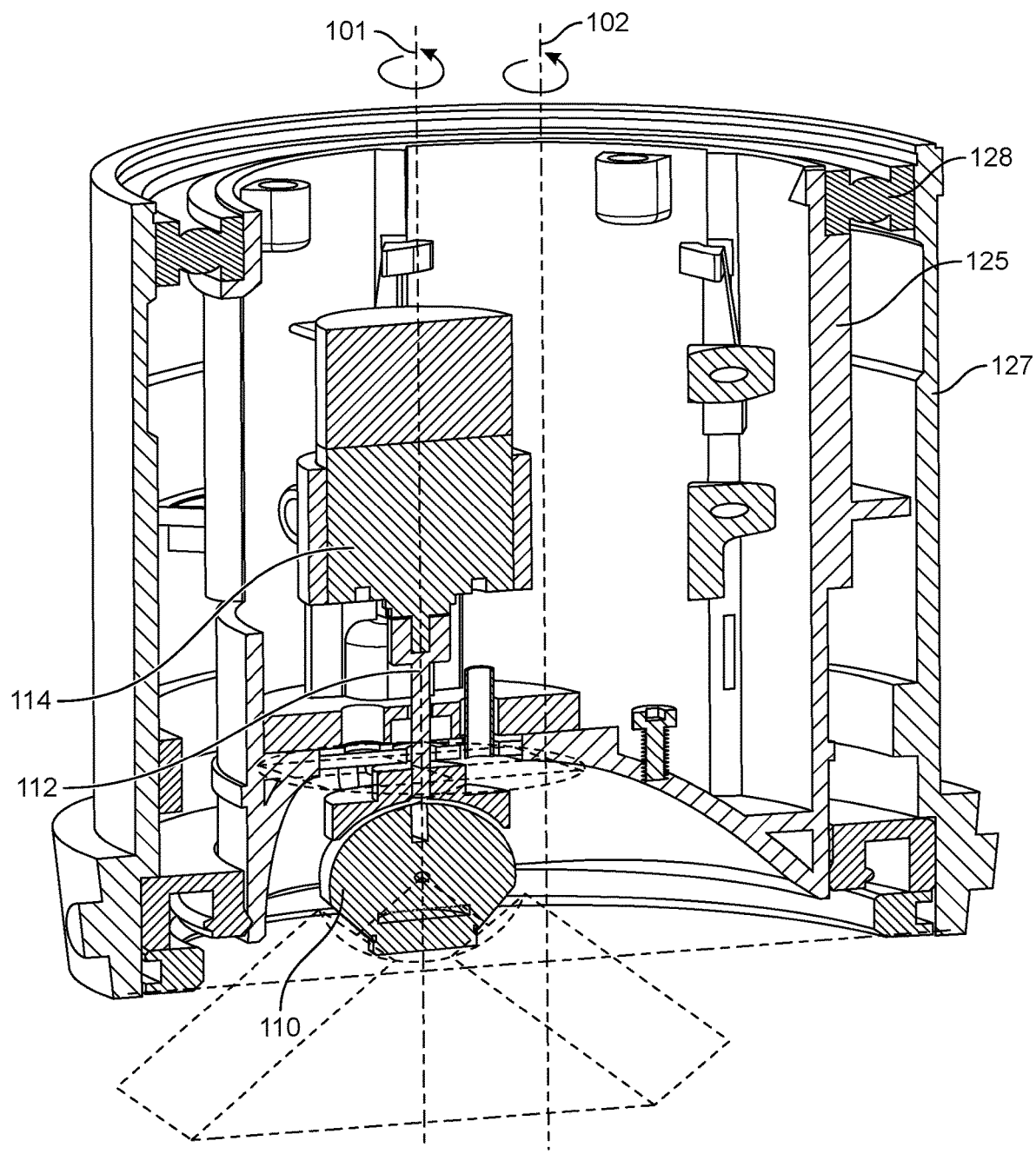

In a second variation (e.g., as shown in FIGS. 1A and 2C-2D), the first and second axes can be offset and parallel or substantially parallel (e.g., within a threshold angle, such as 1°, 2°, 5°, etc.). However, the first and second axes can have any other suitable arrangement relative to one another and to the system.

Figure 7A:
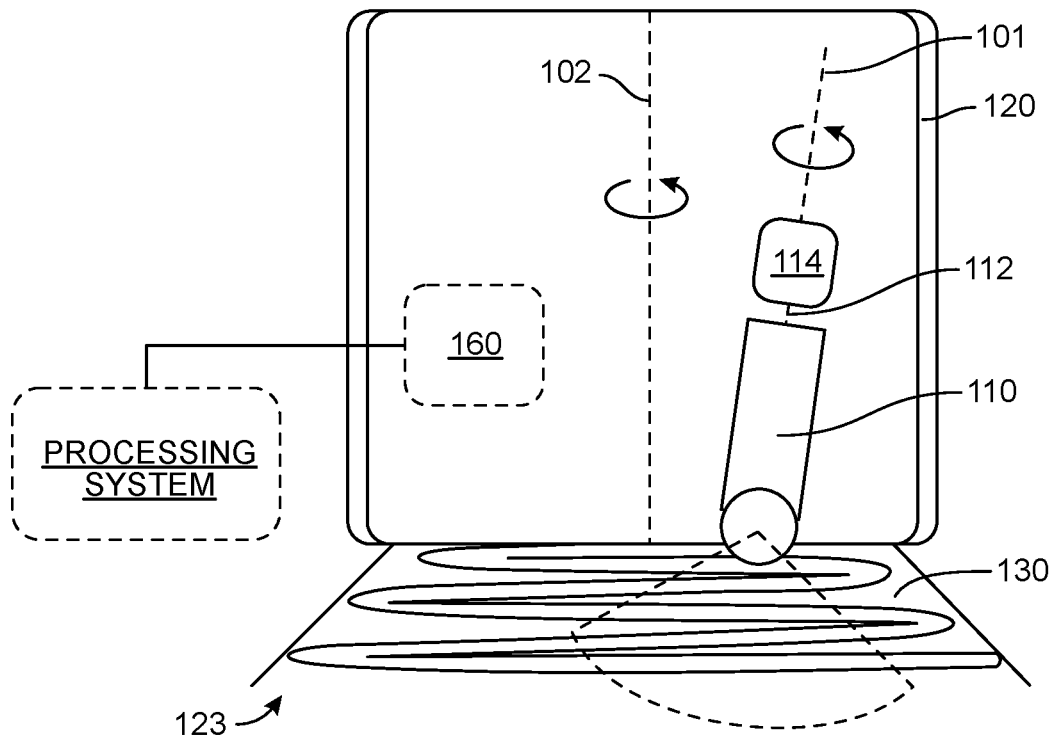
FIGS. 7A and 7B depict a cross-sectional view and a bottom view, respectively, of an alternative variation of a portion of an ultrasound system.
Figure 7B:
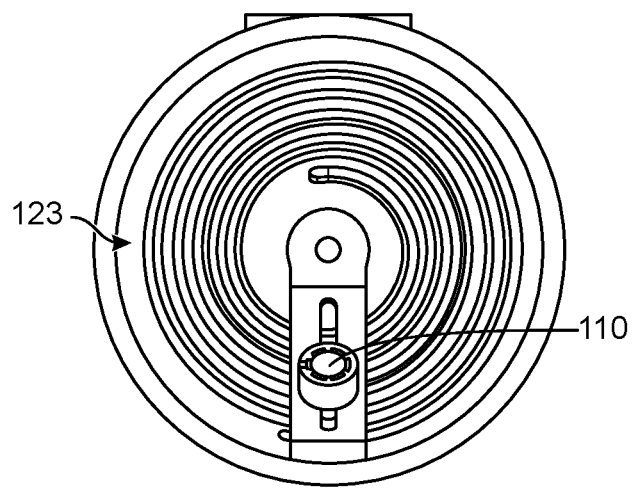
Figure 8A:
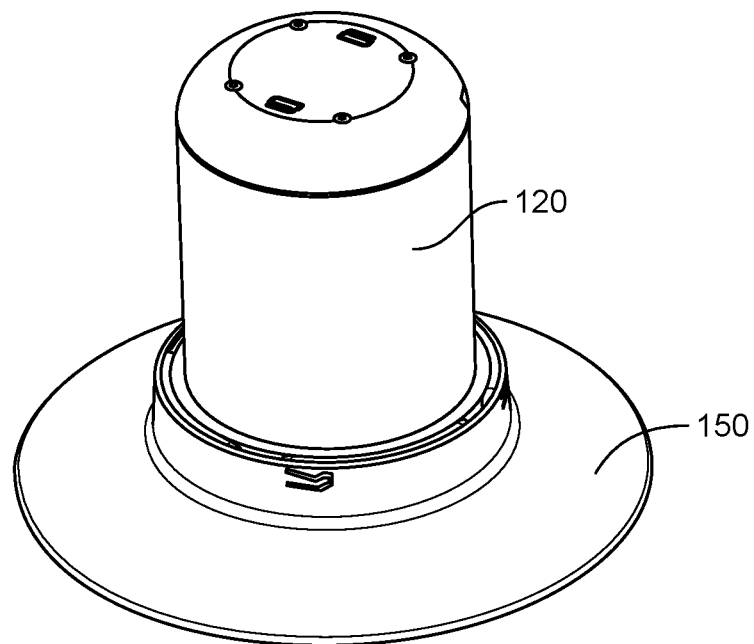
FIGS. 8A-8G depict views of a first specific example of a modular ultrasound system.
Figure 8B:
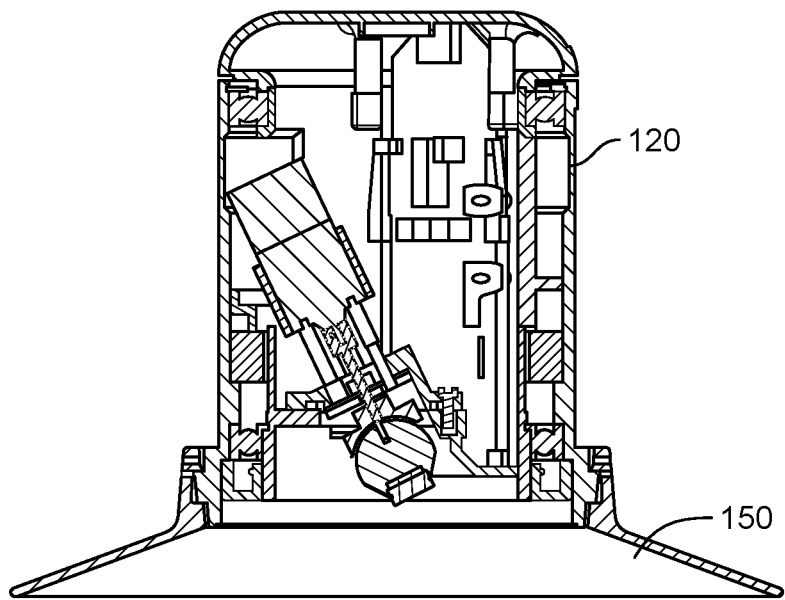
Figure 8C:
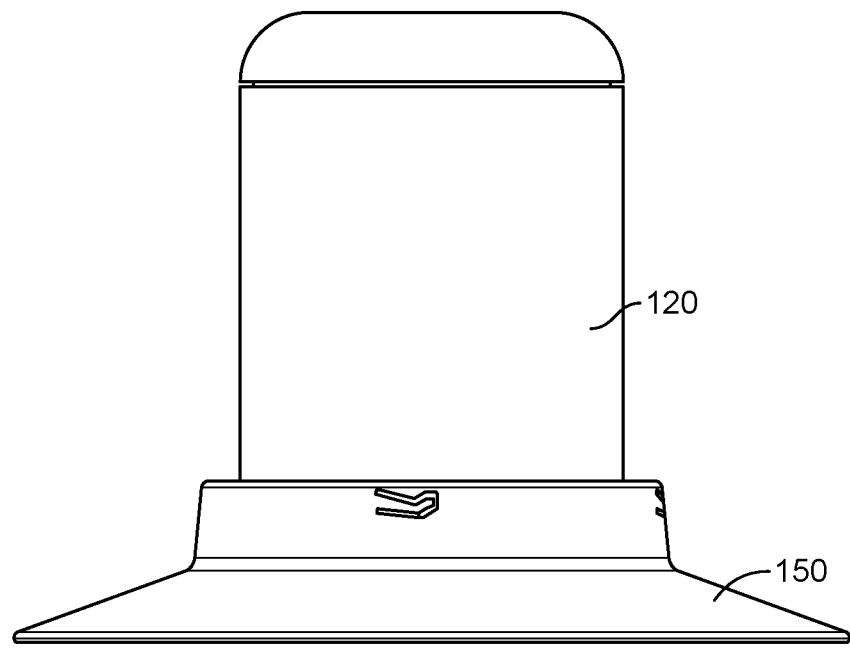
Figure 8D:
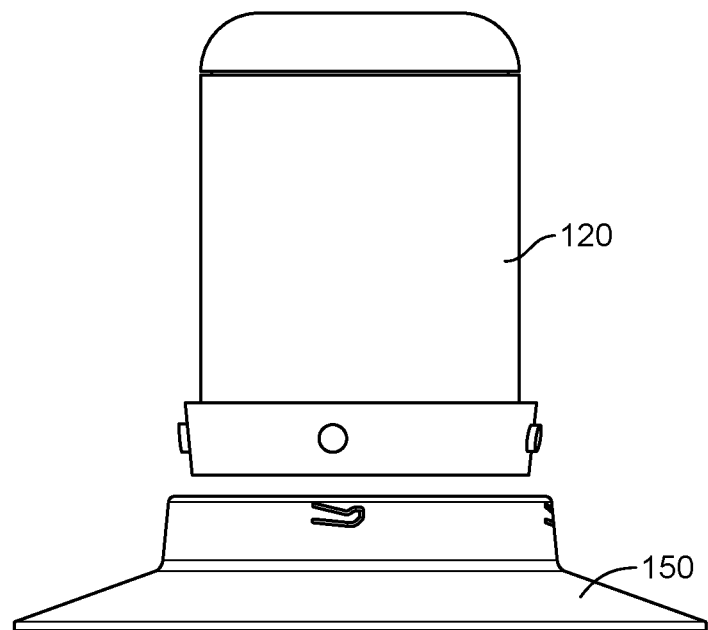
Figure 8E:
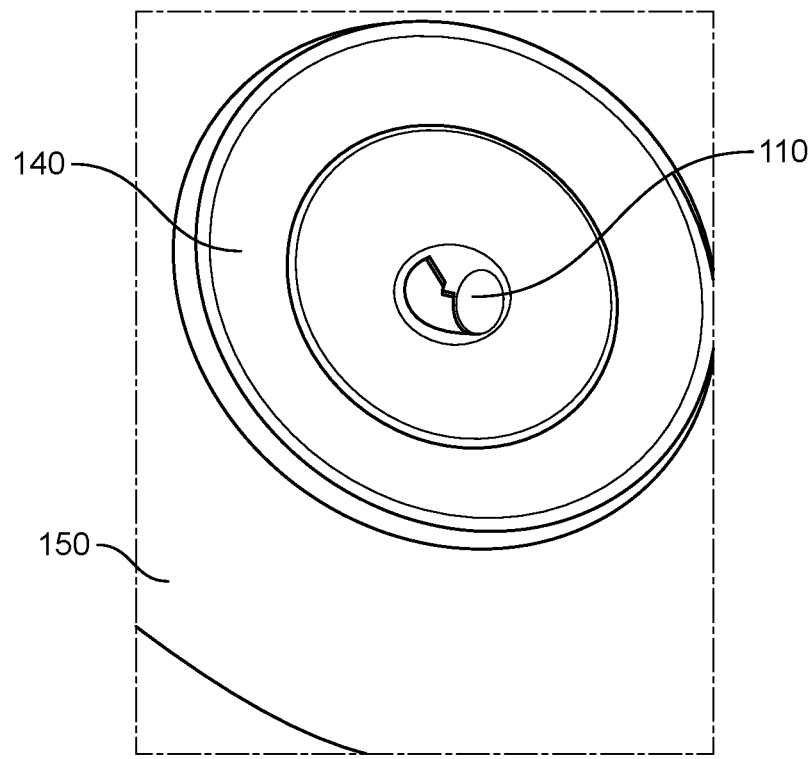
Figure 8F:
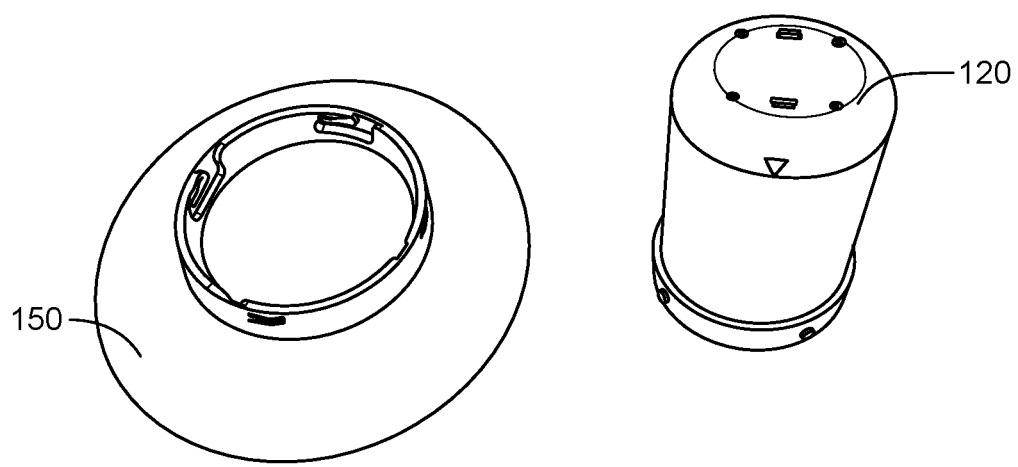
Figure 8G:
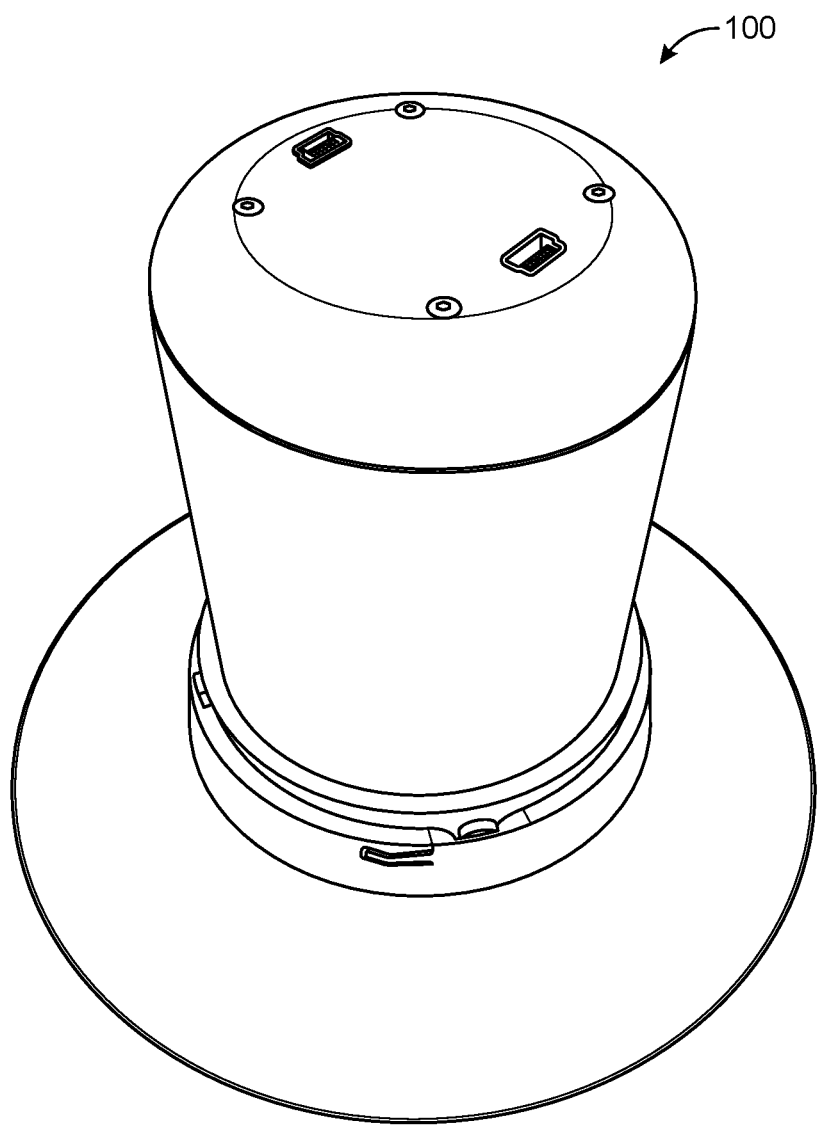

As shown in FIGS. 7A-7B, one or more variations of the housing 120 can include (e.g., within a cupping region) a spiral shaped (e.g., planar spiral, helical, moving non-monotonically along the spiral axis, etc.) track 123 along which the transducer is guided by way of an actuator, thereby allowing the transducer to move along a spiral-shaped scanning path (e.g., over a surface such as a curved or flat surface). The spiral shaped track 123 preferably defines a spiral axis substantially parallel to a major axis of the system (e.g., first axis 101, second axis 102, cylinder axis, longitudinal axis, beam axis such as a central beam axis 103, etc.), but can additionally or alternatively define a spiral axis with any other suitable orientation. In a specific example of this variation, as shown in FIG. 7B, the transducer 110 can be coupled to an actuator's shaft with a coupler (e.g., arm), such that rotation of the coupler causes the transducer 110 to traverse the spiral-shaped scanning path in scanning the tissue of the user. Data produced at each position of the scanning path, due to interaction of the transducer beam with the tissue, can be used to generate 2D, 3D, and/or 4D ultrasound images according to one or more reconstructions processes described in more detail below.

The housing 120 can additionally or alternatively include alignment elements positioned between different housing portions, in order to maintain proper alignment between the housing portions. Additionally or alternatively, the housing 120 and/or any other suitable portion of the system 100 can be configured to provide scanning paths with non-rotational axes of symmetry.

1.3 System—Reservoir and Window

The reservoir 130 of coupling medium is configured to surround a scanning portion of the transducer 110, and functions to provide a fluid (e.g., a material with sufficiently low viscosity) that has a high degree of acoustic transparency to provide proper scanning. In more detail, the coupling medium preferably has a low enough viscosity in order to substantially fill the reservoir and keep air bubbles at an upper region of the reservoir; however, variations of the coupling medium can alternatively comprise any other suitable material (e.g., liquid material, etc.). In one example, the coupling medium can include a natural polymer (e.g., agarose, gelatin). In another example, the coupling medium can include a synthetic polymer. Still alternatively, in other examples, the coupling medium can include a non-hydrogel liquid (e.g., water, etc.) having suitable acoustic transparency characteristics.

In relation to the housing 120 described above, one or more of the first housing portion 125 and the second housing portion 127 can provide or otherwise contain elements that form a boundary of the reservoir, thereby maintaining the coupling medium within desired regions of the system 100. The reservoir boundary (e.g., formed by the housing), as well as any elements within the reservoir, are preferably relatively smooth (e.g., including curved surfaces and interfaces, rather than flat surfaces and angular interfaces, such as shown in FIG. 2D). However, the boundary can additionally or alternatively have any suitable shape. The reservoir boundary (e.g., formed by the housing), as well as any elements within the reservoir, can optionally include coatings (e.g., ultrasound anti-reflection coating, ultrasound absorptive coating, ultrasound dispersive coating, etc.). The smooth and/or coated elements can function to minimize spurious signals caused by ultrasound reflection.

In relation to the reservoir, the system 100 also preferably includes a window 140 (e.g., rigid or flexible membrane, aperture, etc.), which can optionally be configured to conform to a body region of a user during operation and/or form a boundary of the reservoir. The window is preferably positioned proximal to the cupping region 122 of the housing 120 described above in order to form a boundary of the reservoir, and is preferably retained against a skin surface (or other body surface) of the user in a manner that provides coupling between the ultrasound beam of the transducer 110 and the body of the user, more preferably without producing air gaps or bubbles at the interface between the system and the user (e.g., by defining a concavity configured to accept a user's breast). Alternatively, the window can be convex (e.g., to accommodate the ultrasound transducer and/or beam) and/or have any other suitable shape.

Similar to the coupling fluid, the window is preferably composed of a material having a high degree of acoustic transparency to facilitate proper scanning of the tissue volume; however, the window can alternatively be composed of any other suitable material. The window can optionally include coatings (e.g., ultrasound anti-reflection coating), which can function to decrease window interference with the ultrasound beam (e.g., increase direct ultrasound transmission through the window). The window can additionally or alternatively be processed or otherwise omit sharp edges at boundaries of the window, in order to prevent undesired characteristics for scanning. The material of the window is preferably rigid, but can additionally or alternatively be compliant and/or flexible (e.g., flexible polymer, such as a silicone), in relation to coupling medium delivery and/or pressurization aspects described in more detail below; however, the window 140 can alternatively have any other suitable characteristics. Furthermore, the window can be used in cooperation with an ultrasound-appropriate gel applied directly to the skin surface (or other body region) of the user, in order to provide an air or bubble-free interface.

The coupling medium is preferably sealed within the reservoir. For example, the system can include a gasket (e.g., between the housing and window, between elements of the housing, etc.) to prevent leakage of coupling medium from the reservoir. The reservoir can alternatively be open (e.g., include an aperture for filling and/or emptying the reservoir).

As noted above, the system 100 can additionally include a coupling medium delivery system that interfaces with the reservoir, in order to provide a means for delivering and/or removing coupling medium from the reservoir. Additionally or alternatively, the system can include a coupling medium delivery system that transmits coupling medium (e.g., ultrasound gel) directly to an interface between the system 100 and the body of the user. Additionally or alternatively, the system can include a coupling medium pressure modulating system that is independent from or otherwise coincides with a fluid delivery system, such that a pressure applied to the tissue of the user by the system 100 can be dynamically controlled. In one application, pressurization of the coupling medium can function to eliminate air bubbles or gaps between the system and the body region of the user to enhance scanning by increasing pressure to press the window 140 against the body region. Additionally or alternatively, in another application, modulation of pressure can be used to control positioning of the tissue body of the user relative to the system, in order to provide a means for improving repeatability of scanning during multiple scanning operations (e.g., scanning operation spaced apart in time). Additionally or alternatively, in another application, modulation of pressure can be used to controllably deform the tissue body in order to provide data for characterization of the tissue according to elastosonography methods (e.g., in terms of tissue mass stiffness, tissue mass density, characterization of benign masses, characterization of malignant masses, etc.). However, pressurization can additionally or alternatively serve any other suitable purpose.

The coupling medium delivery system and/or coupling medium pressure modulation system can thus include any one or more of: a pump, channels for transmission of coupling medium, pressure sensors to detect appropriate pressures within the system for pressure control, flow sensors, and any other suitable element(s).

1.4 System—Modularity and Positioning Elements

Figure 9A:
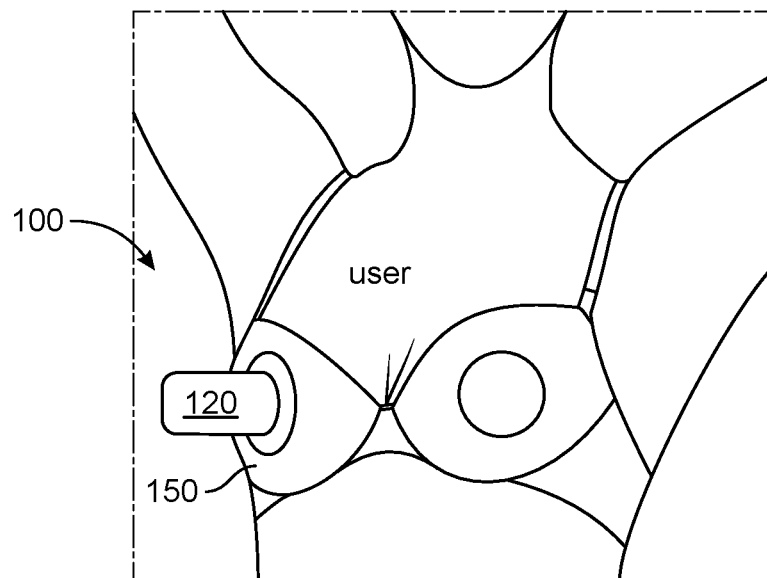
FIG. 9A depicts a user wearing a second specific example of a modular ultrasound system in an assembled configuration.
Figure 9B:
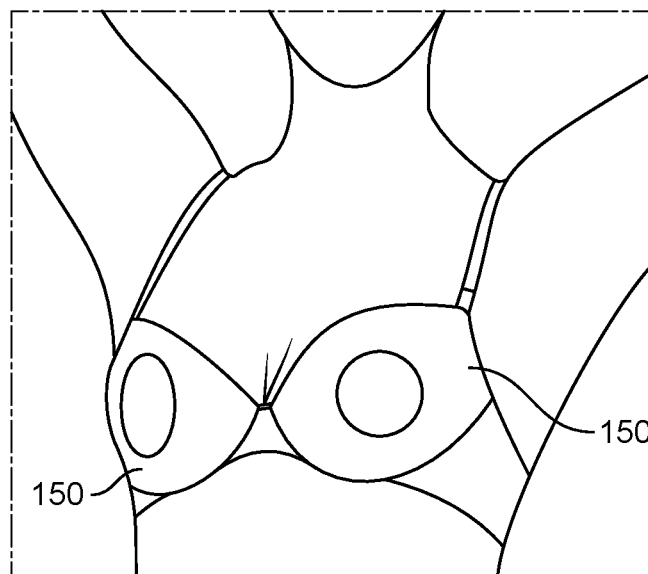
FIG. 9B depicts the user wearing a portion of the second specific example of the modular ultrasound system in a disassembled configuration
Figure 10A:
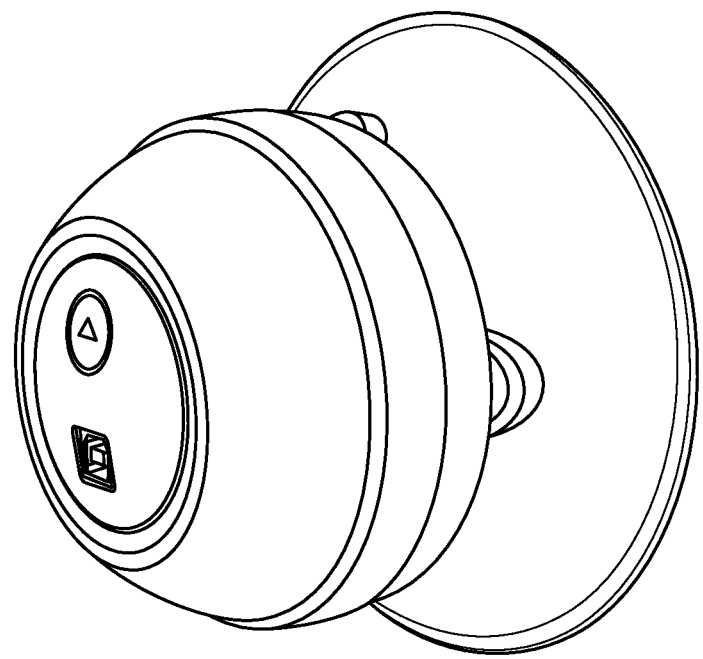
FIGS. 10A-10D depict perspective views of a third specific example of a modular ultrasound system.
Figure 10B:
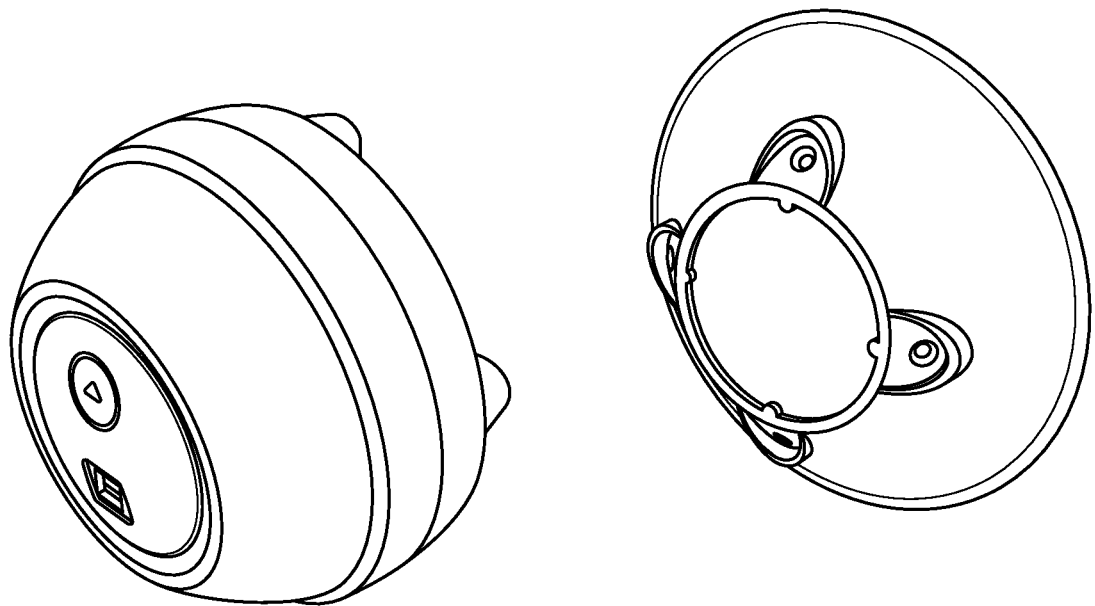
Figure 10C:
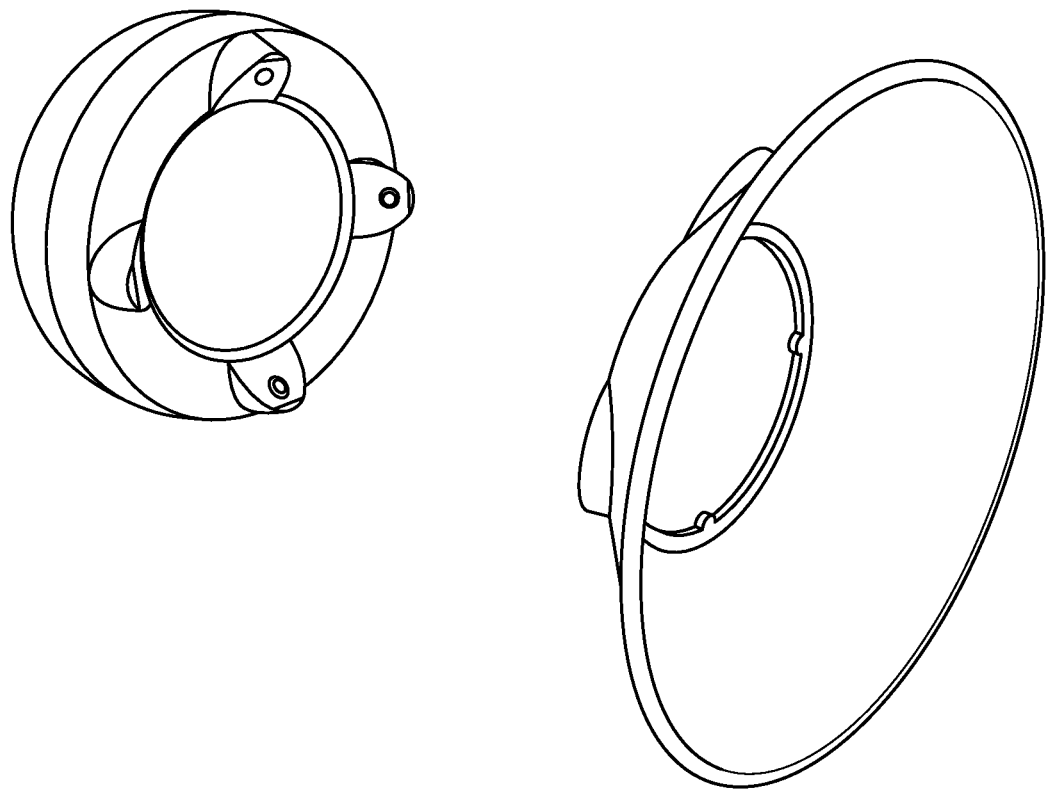
Figure 10D:
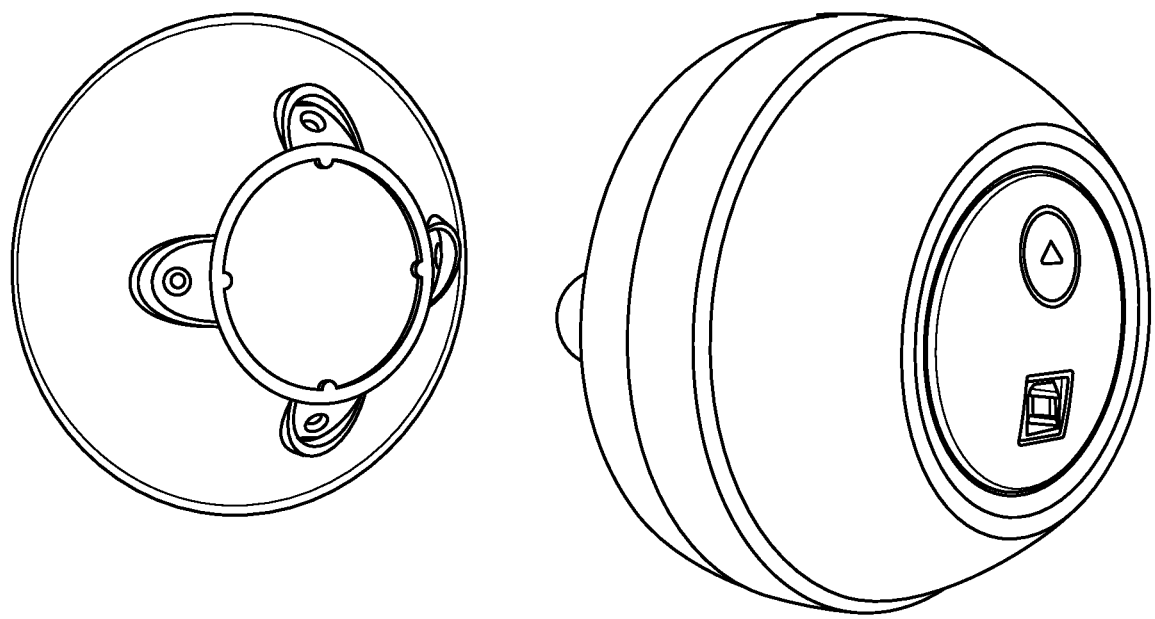
Figure 11A:
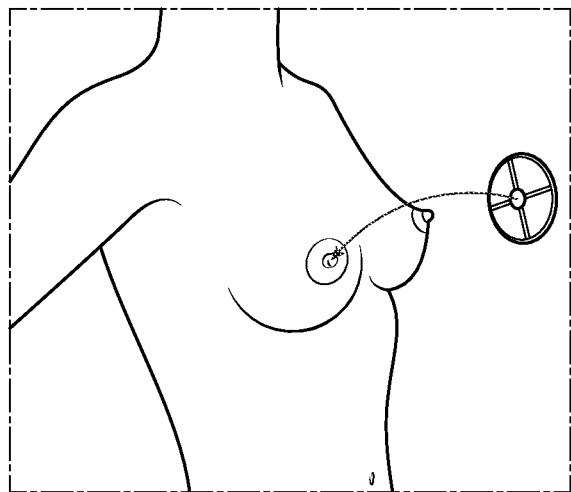
FIGS. 11A-11D depict perspective views of a specific example of placing a modular ultrasound system on a breast.
Figure 11B:
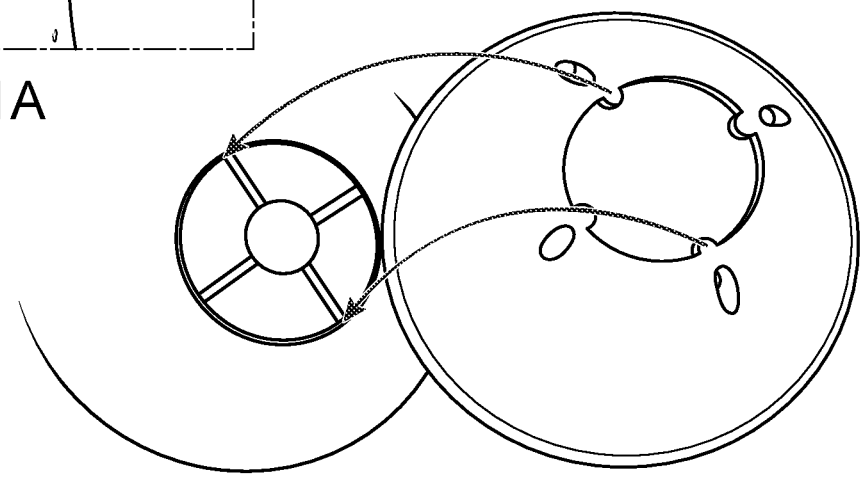
Figure 11C:
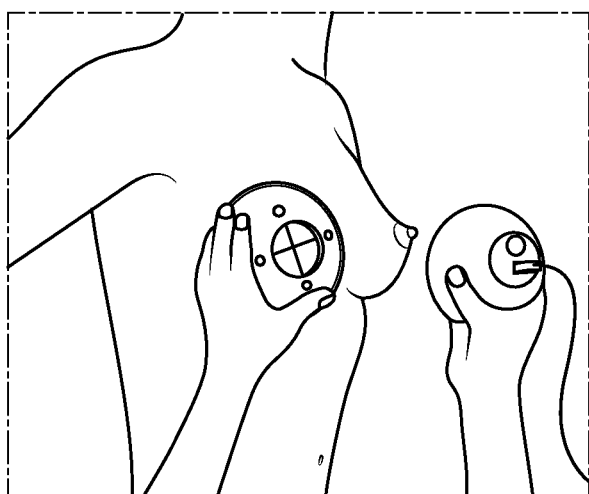
Figure 11D:
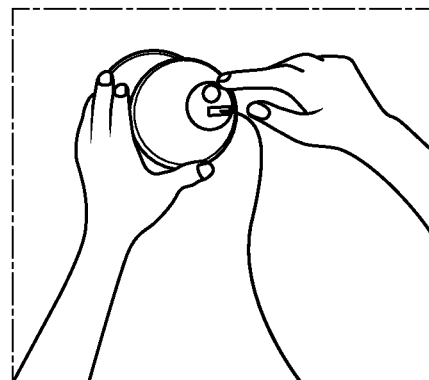

The positioning portion 150 can be incorporated with or otherwise interface with the window 140, and functions to facilitate reliable and repeatable positioning of the scanner assembly relative to the body region of the user. The positioning portion 150 can additionally or alternatively be a portion of a modular system 100 that promotes hygienic use of the system (e.g., in terms of disposability, in terms of washability, etc.). For example, the modular system can include a scanner module and a positioner module (e.g., including the positioning portion 150). The positioning portion 150 can include one or more alignment features that promote proper placing of the position portion 150 at the body region of the user, and/or proper positioning of the scanning assembly relative to the body region of the user. In one variation, the positioning portion 150 can include an opening or region configured to receive the nipple of the user, such that the positioning portion 150 is aligned with the nipple of the user. Additionally or alternatively, the positioning portion 150 can include features that lock or otherwise align the scanning assembly in place, in order to promote repeatable scanning. The positioning portion 150 can be a one-size-fits-all (or one-size-fits-most) element that increases versatility of the system 100 for a wide variety of body types or tissue types. However, the positioning portion 150 can alternatively be a customizable portion of the system that can be designed with sizes and/or morphologies specific to an individual user. For example, the positioning portion 150 can be an item of clothing (e.g., brassiere, such as shown in FIGS. 9A-9B) and/or other wearable element.

As noted above, the positioning portion 150 can interface with or otherwise be incorporated with the window 140, and preferably comprises a material with a high degree of acoustic transparency. The positioning portion 150 can be composed of a material with suitable biodegradation characteristics (e.g., hydro- and/or oxo-degradable polymer), in order to prevent reusability and promote disposability of the positioning portion 150. Additionally or alternatively, the positioning portion 150 can be composed of a material that can be washed, in order to promote reusability of the positioning portion 150. In variations wherein the positioning portion 150 is disposable, units of the positioning portion 150 can be provided to the user according to a subscription model that promotes regular scanning of the tissue of the user at a desired frequency. The system can optionally be configured to be shared by multiple users. For example, in a clinical setting, a new, disposable positioning portion 150 (and/or other tissue-contacting elements of the system) can be used for each patient to be examined. The positioning portion 150 can be affixed to the housing 120 before examination, and can be detached and discarded after the examination.

In one variation, the scanner module and positioner module each include a reservoir 130 containing ultrasound coupling material (e.g., as described above regarding the reservoir). The two reservoirs are preferably arranged to be retained against each other when the modules are attached, but can alternatively have any other suitable arrangement. However, the system can include only a single reservoir 130 (e.g., in the scanner module, in the positioner module) or include any other suitable number of reservoirs in any other suitable arrangement.

The modules preferably include fasteners configured to attach the modules (e.g., retain them against each other). For example, the scanner module can include a first fastener element (e.g., on the scanner module housing), and the positioner module can include a second, complementary fastener element configured to fasten to the first fastener element, cooperatively forming the fastener(s). The fasteners can include screw mounts, bayonet mounts, friction fits, latches, hook-and-loop fastener elements, adhesives, magnets, van der Waals force elements, and/or any other suitable fastener elements. The fasteners preferably enable facile, reversible, and repeatable attachment of the modules, but can alternatively cause irreversible fastening, un-repeatable fastening, and/or attach the modules in any other suitable manner.

The positioning portion 150 can, however, be configured in any other suitable manner. Examples of a modular system 10o having a positioning portion 150 that interfaces with the housing 120 with a reversible interlocking mechanism are shown in FIGS. 8A-8G. An alternative example of a modular system is shown in FIGS. 10A-10D.

1.5 System—Electronics

The electronics subsystem 160 is configured to facilitate actuation of the transducer and/or portions of the housing by one or more actuators and to facilitate acquisition of scanning data from the body region of the user. As such, the electronics subsystem 160 can include one or more of: analog front end (AFE) circuitry, field programmable gate array (FPGA) circuitry, microcontrollers, memory, a linking interface (e.g., wired linking interface 161, such as shown in FIG. 5, wireless linking interface), a power management subsystem, a battery (e.g., non-rechargeable battery, rechargeable battery) interfacing with the power management subsystem, and any other suitable electronics.

The electronics subsystem 160 can be split among any suitable number of boards, for instance, to control for vibration and/or noise associated with signal generation and/or transmission. Furthermore, the electronics subsystem 160 is preferably contained within the housing 120; however, the electronics subsystem 160 can alternatively have one or more portions situated outside of the housing 160.

The system 100 can, however, include any other suitable elements or interface with any other suitable elements that facilitate scanning and/or processing of scanning data. For instance, the system 100 can include or otherwise communicate with computing systems (e.g., cloud computing systems, remote servers, etc.) configured for image processing of data produced by the system 100. The system 100 can also be configured to interface with or be accompanied by application software (e.g., of a native application executing on a mobile computing device, of a web application, etc.) that allows a user or other operator to interface with the system 100 using a wired or wireless connection, as described in more detail in Section 2 below. As such, as a person skilled in the art will recognize from the previous detailed description and from the figures, modifications and changes can be made to the system 100 without departing from the scope of this system 100.

2. Method

A method 200 for tissue scanning can include one or more of: providing an embodiment, variation, or example of the system 100 described in Section 1 above to a user; receiving control inputs from a user or other operator of the system; receiving scanning data; reconstructing image data upon processing of the scanning data; and providing information derived from reconstruction of the image data to the user or other operator. The method 200 can include repeated steps at multiple points in time, in association with regular (or irregular) scanning of tissue, to promote early detection of tissue abnormalities (e.g., cancer). For instance, longitudinal data collected over time, associated with repeat scans of the tissue of the user, can allow for tracking of changes in detected masses, growth in detected masses, and/or any other change in the tissue body(ies) being monitored, in relation to normal variability of the tissue body(ies) being scanned, or variability in placement of the system onto the user for each scanning operation.

The method 200 can be implemented using embodiments, variations, or examples of elements of the system described in Section 1 above, or can additionally or alternatively be implemented, at least in part, using any other suitable system.

In relation to scanning of a tissue body, the method 100 can include generation of A-mode scans, B-mode scans, and/or any other suitable type of scanning data, as described above. Furthermore, scanning can include providing appropriate commands to actuators of the system 100, to drive a transducer of the system along a desired scanning path (e.g., by way of actuators and positional encoders). Thus, scanning can include generation of 2D, 3D, and/or 4D data of a tissue body and/or a region of interest of the tissue body. Furthermore, scanning can be associated with a suitable data acquisition rate (e.g., associated with non-real-time image processing and viewing, associated with real-time image processing and viewing), in order to provide enhanced images (e.g., through averaging operations, through frequency and/or spatial compounding operations, etc.).

In relation to receiving control inputs, the method 100 can include providing an interface between the system 100 and a controller configured to receive inputs from a user or other operator of the system. Providing the interface can include providing a web-implemented platform, controller device platform, mobile device application platform, and/or any other suitable platform that allows a user or other entity to provide inputs to the system. The application platform can allow the user or other entity to communicate with the system (e.g., over a wireless and/or wired connection) to initiate, terminate, or restart a scanning protocol. The application platform can additionally or alternatively provide a user or other entity with a progress status along a scanning protocol. The application platform can additionally or alternatively provide a user or other entity with a success or failure status of a scanning protocol. The application platform can additionally or alternatively facilitate transmission of scanning data to a processing system (e.g., cloud-computing system, remote server, etc.). However, receiving scanning data and/or control inputs can additionally or alternatively be implemented in any other suitable manner.

In relation to reconstructing image data, the method 200 can include performing near-real time and/or non-real time processing of scanning data. In one variation, the method 200 may omit real-time image processing, in a system configuration that does not display near-real time images to the user during a scanning protocol. As such, processing can provide enhanced images using one or more of: averaging operations, frequency compounding operations, denoising operations, compression operations (e.g., wavelet transformation operations, thresholding operations), and any other suitable image processing operations. Processing and analysis of ultrasound images (e.g., 2D, 3D, 4D ultrasound images) and/or raw ultrasound signals (e.g., high-frequency signals) can allow for characterization of tissue in multiple planes, for differentiation of benign from malignant masses.

In relation to providing information derived from reconstruction of the image data, the method can include implementing the application platform to provide one or more of: image analyses (e.g., through a mobile device application), reports regarding detection of abnormal masses, reports regarding changes in a previously detected abnormal mass, suggestions for treatment of a detected mass, educational information pertaining to a detected mass, and any other suitable information derived from processing of scanning data generated according to the method 200. Providing information can additionally or alternatively include sharing image data or other data to another entity (e.g., radiologist, teleradiologist, etc.) for further processing or analysis, wherein additional information from the entity can also be provided to the user by way of the application platform. Providing information can additionally or alternatively include allowing a user to control the type(s) of information provided to him/her, allow a user to view historical scanning information (e.g., scan dates, reports), allow a user to be reminded to undergo upcoming scans, and/or guide a user through calibration of the system.

The method can, however, include any other suitable steps or blocks that enable scanning and/or processing of scanning data.

Benefits

The system 100 and/or method 200 can confer several benefits. Since real-time diagnostic ultrasound imaging and display is not necessarily required, it can be possible to forgo using a large transducer array, which can reduce hardware complexity required for beamforming and/or the number of transmit and receive channels. As a result, all the required electronics (e.g., analog transmit and receive electronics, low-cost FPGA and microcontroller for digital signal processing and I/O operations, etc.) can be integrated in a small PCB. A transducer can be mechanically moved in an oil-filled repository in two orthogonal planes to scan over a large surface area and later generate a 3D ultrasound volume. Since data acquisition rate is not necessarily limited by display frame rate, image enhancement techniques can be used during data capture such as averaging and spatial compounding by scanning over an area multiple times and different angles and combining overlapping images. The captured raw data can be buffered to flash memory and/or to the connectivity interface. Wired (e.g., USB) and/or wireless (e.g., Bluetooth, Wi-Fi, cellular data, etc.) connections can be included for control and/or data transfer. The stored raw RF data can be post-processed later at an external computing system (e.g., remote server) after the data is transferred to the external computing system. This can function to offload advanced signal processing from the FPGA of the system to the external computing system, which can help to reduce the processing power required in the system, thereby reducing both the cost and volume required, which can enable a compact unit.

The system can be designed to produce repeatable ultrasound scans (e.g., for longitudinal monitoring of changes in tissue, such as breast tissue). Such temporal information, not available from many typical imaging systems, can facilitate the diagnosis of abnormalities, which can enable detection of potential tumors at earlier stages. To enable such repeatability, the system preferably includes a positioning accessory to secure the ultrasound scanner relative to breast tissue in a reproducible position and/or pressure (e.g., as shown in FIGS. 11A-11D). Sensors (e.g., inertial sensors) can be used to track position, angle, and/or motion, and/or to correct for variations during and between scans. The system can additionally or alternatively include integrated sensors (e.g., 9-DOF sensor package) on the scanning device and/or positioning accessory to facilitate consistent positioning and orientation. A client of a user device (e.g., mobile app) can optionally connect to the system (e.g., via Bluetooth), which can enable visual feedback and guidance for consistent positioning. The system can optionally include a locking mechanism, which can fasten the scanner and the positioning accessory in the same orientation relative to the body. Also, visual, optical, and/or acoustic landmarks can be used in the positioning accessory and/or the window to register and align the positioning accessory (e.g., and thereby the system) relative to the designated parts of the body (e.g., nipple). In addition, volumetric ultrasound images can be acquired by automatically moving the transducer over the surface of the tissue (e.g., in a predefined scan pattern), which can be programmed and controlled electronically. One or more (e.g., two) position encoders can be used to record the scanning position of the transducer in real-time. By reconstructing the captured scans with the position data, a 3D ultrasound image can be generated and accurately mapped on the tissue volume. The automation of the scan mechanism can enable hands-free operation of the scanner, which can reduce or eliminate operator error, resulting in repeatable imaging of tissue. However, the system and method can confer any suitable benefit(s).

The system 100 and method 200 of the preferred embodiment and variations thereof can be embodied and/or implemented at least in part in the cloud and/or as a machine configured to receive a computer-readable medium storing computer-readable instructions. The instructions are preferably executed by computer-executable components preferably integrated with the system and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in a flowchart or block diagrams can represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession can, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. An ultrasound system comprising:
    a scanner module, comprising:
        a scanner housing, comprising a longitudinal axis in a direction towards a portion of a skin of a user and a first fastener element,
        an ultrasound transducer within the scanner housing, the ultrasound transducer comprising a central beam axis, wherein an angle between the central beam axis and the longitudinal axis is less than 45°,
        a first actuator within the scanner housing, the first actuator coupling the ultrasound transducer to the scanner housing about the longitudinal axis, wherein the ultrasound transducer sweeps a curved path around the longitudinal axis during rotation, and
        an electronics module within the scanner housing; and
    a positioner module comprising a second fastener element, a shape configured to enclose an ultrasound coupling material by partially contacting the portion of a skin of a user, and an aperture to expose a volume of tissue to the ultrasound transducer,
    wherein the first and second fastener elements cooperatively couple together the scanner module and the positioner module.

2. The system of claim 1, further comprising a reservoir attached to the positioner module, the reservoir configured to partially receive the ultrasound coupling medium; and
    wherein the central beam axis extends through the reservoir.

3. The system of claim 2, wherein the reservoir is configured to seal in the ultrasound coupling medium.

4. The system of claim 2, wherein the positioner module comprises a membrane configured to form a boundary of the reservoir.

5. The system of claim 1, wherein the positioner module comprises a biodegradable material.

6. The system of claim 1, wherein the positioner module comprises a frustoconical region configured to align the system to a breast of a user.

7. The system of claim 1, wherein the central beam axis is offset from and parallel to the longitudinal axis.

8. The system of claim 1, further comprising a second actuator in the housing, the second actuator coupled to the ultrasound transducer.

9. The system of claim 8, wherein the second actuator is configured to translate the ultrasound transducer along a radial direction relative to the longitudinal axis.

10. The system of claim 8, wherein the ultrasound transducer comprises a linear array of ultrasound transducer elements.

11. The system of claim 1, wherein the positioner module comprises an ultrasound anti-reflection coating.

12. The system of claim 1, wherein at least one of the scanner module and the positioner module comprises at least one of: a marking, a position sensor, and a position encoder operable to promote repeatability of scanning of a user body region.

13. The system of claim 1, wherein the positioner module comprises a membrane.

14. The system of claim 13, wherein the membrane is configured to conform to a body region of a user.

* * * * *